United States Patent
Freedman et al.

(10) Patent No.: US 11,127,278 B2
(45) Date of Patent: Sep. 21, 2021

(54) HAND HYGIENE AND SURGICAL SCRUB SYSTEM

(71) Applicant: Intelligent Observation, Inc., Miami, FL (US)

(72) Inventors: Seth Freedman, Miami, FL (US); Mike Cronin, Crosshaven (IE); Michael S. Beck, Bull Valley, IL (US)

(73) Assignee: Intelligent Observation, Inc., Miami, FL (US)

( * ) Notice: Subject to any disclaimer, the term of this patent is extended or adjusted under 35 U.S.C. 154(b) by 0 days.

(21) Appl. No.: 16/252,532

(22) Filed: Jan. 18, 2019

(65) Prior Publication Data
US 2019/0228640 A1    Jul. 25, 2019

Related U.S. Application Data

(60) Provisional application No. 62/625,223, filed on Feb. 1, 2018, provisional application No. 62/619,549, filed on Jan. 19, 2018.

(51) Int. Cl.
*G08B 23/00* (2006.01)
*G08B 21/24* (2006.01)
(Continued)

(52) U.S. Cl.
CPC .......... *G08B 21/245* (2013.01); *G08B 21/18* (2013.01); *G16H 40/20* (2018.01); *A47K 5/1217* (2013.01); *G09B 19/0076* (2013.01)

(58) Field of Classification Search
CPC ...... G08B 21/245; G08B 21/18; G16H 40/20; A47K 5/1217; G09B 19/0076
See application file for complete search history.

(56) References Cited

U.S. PATENT DOCUMENTS

| | | | | |
|---|---|---|---|---|
| 7,576,650 | B1* | 8/2009 | Ghaffari | G05B 19/00 340/572.1 |
| 7,800,500 | B2* | 9/2010 | Batra | G01S 13/74 340/572.1 |

(Continued)

FOREIGN PATENT DOCUMENTS

WO    WO-2015/061718 A1    4/2015

OTHER PUBLICATIONS

Arslan et al., The performance bounds of RFID protocols in wireless channel for ISO 18000-3 standard (Year: 2012).*

(Continued)

*Primary Examiner* — Quang Pham
(74) *Attorney, Agent, or Firm* — Steven J Rocci P.C.

(57) ABSTRACT

A hand hygiene monitoring system is provided. The system includes a wearable tag device coupled to a user, and a reader device communicably coupled to the wearable tag device. The reader device is configured to detect a presence of the wearable tag device by receiving a first frequency message comprising a user identifier from the wearable tag device. The reader device is further configured to transmit a second frequency message to the wearable tag device requesting event log data. The second frequency has a higher frequency than the first frequency. The reader device is further configured to receive an event log data message from the wearable tag device at the second frequency, and to determine whether the wearable tag device has logged a wash station encounter within a configurable time period based on the event log data message.

17 Claims, 14 Drawing Sheets

(51) Int. Cl.
*G08B 21/18* (2006.01)
*G16H 40/20* (2018.01)
*A47K 5/12* (2006.01)
*G09B 19/00* (2006.01)

(56) References Cited

U.S. PATENT DOCUMENTS

| | | | | |
|---|---|---|---|---|
| 8,094,029 | B2* | 1/2012 | Ortiz | G16H 40/20 340/573.1 |
| 9,317,725 | B1* | 4/2016 | Van Eeden | G06K 19/0712 |
| 2007/0096876 | A1* | 5/2007 | Bridgelall | H04B 7/0802 340/10.1 |
| 2007/0126556 | A1* | 6/2007 | Subramanian | G06K 19/0723 340/10.4 |
| 2008/0122584 | A1* | 5/2008 | Itasaki | G06K 19/0723 340/10.51 |
| 2008/0140416 | A1 | 6/2008 | Shostak | |
| 2008/0204194 | A1* | 8/2008 | Haar | G06K 7/0008 340/10.1 |
| 2008/0266103 | A1* | 10/2008 | Chen | G06K 7/0008 340/572.7 |
| 2009/0045921 | A1* | 2/2009 | Nelson | G06K 7/10297 340/10.2 |
| 2009/0045923 | A1* | 2/2009 | van Eeden | G06K 7/10297 340/10.3 |
| 2009/0051545 | A1* | 2/2009 | Koblasz | G08B 21/245 340/573.1 |
| 2009/0195385 | A1* | 8/2009 | Huang | G16H 40/20 340/572.1 |
| 2009/0201116 | A1* | 8/2009 | Orihara | H01Q 1/38 336/200 |
| 2009/0267765 | A1* | 10/2009 | Greene | G06K 7/0008 340/568.1 |
| 2010/0026467 | A1* | 2/2010 | Van Eeden | G06K 7/0008 340/10.5 |
| 2010/0117836 | A1* | 5/2010 | Seyed Momen | G01S 1/70 340/573.1 |
| 2010/0123560 | A1* | 5/2010 | Nix | H04Q 9/00 340/10.4 |
| 2010/0164728 | A1 | 7/2010 | Plost | |
| 2010/0277284 | A1* | 11/2010 | Brown | G06K 7/10079 340/10.3 |
| 2010/0321180 | A1* | 12/2010 | Dempsey | G16H 40/20 340/539.12 |
| 2010/0328076 | A1* | 12/2010 | Kyle | G16H 40/67 340/573.1 |
| 2010/0328443 | A1* | 12/2010 | Lynam | G06K 9/036 348/77 |
| 2011/0095892 | A1* | 4/2011 | Hong | H01Q 21/065 340/572.7 |
| 2011/0281522 | A1* | 11/2011 | Suda | G06Q 10/0833 455/41.2 |
| 2012/0062382 | A1* | 3/2012 | Taneff | G08B 21/245 340/573.1 |
| 2012/0112906 | A1* | 5/2012 | Borke | G08B 21/245 340/539.13 |
| 2012/0119883 | A1* | 5/2012 | Bekritsky | G06K 7/0008 340/10.4 |
| 2012/0212582 | A1 | 8/2012 | Deutsch | |
| 2012/0256742 | A1 | 10/2012 | Snodgrass et al. | |
| 2013/0120120 | A1* | 5/2013 | Long | G06K 7/01 340/10.5 |
| 2013/0122807 | A1 | 5/2013 | Tenarvitz et al. | |
| 2013/0133762 | A1 | 5/2013 | Snodgrass | |
| 2014/0022069 | A1* | 1/2014 | Lichtenegger | B60C 23/0449 340/447 |
| 2014/0218173 | A1* | 8/2014 | Long | G06K 17/00 340/10.1 |
| 2014/0266692 | A1* | 9/2014 | Freedman | G08B 21/245 340/539.11 |
| 2014/0375457 | A1 | 12/2014 | Diaz | |
| 2015/0127365 | A1* | 5/2015 | Rizvi | G02B 27/017 705/2 |
| 2015/0161874 | A1* | 6/2015 | Thyroff | G08B 25/10 340/539.11 |
| 2015/0280789 | A1* | 10/2015 | Hussain | H04B 5/0037 455/41.1 |
| 2015/0379795 | A1* | 12/2015 | Wu | G07C 9/00309 340/5.61 |
| 2016/0026832 | A1* | 1/2016 | Wadman | G06F 16/285 340/10.1 |
| 2016/0140831 | A1* | 5/2016 | Hermann | G08B 21/245 340/573.1 |
| 2016/0180695 | A1 | 6/2016 | Levchenko et al. | |
| 2016/0216769 | A1* | 7/2016 | Goetz | G06F 3/017 |
| 2016/0267772 | A1* | 9/2016 | Iseri | G08B 21/245 |
| 2016/0275779 | A1* | 9/2016 | Hajdenberg | G08B 21/245 |
| 2016/0320468 | A1 | 11/2016 | Crombez et al. | |
| 2016/0380678 | A1* | 12/2016 | McManus | H04B 1/40 455/73 |
| 2017/0040811 | A1 | 2/2017 | Dryer et al. | |
| 2017/0093464 | A1* | 3/2017 | Karandikar | H04B 5/0025 |
| 2017/0116443 | A1* | 4/2017 | Bolic | H02J 50/90 |
| 2017/0180009 | A1* | 6/2017 | McManus | H04B 5/0062 |
| 2017/0256155 | A1* | 9/2017 | Sengstaken, Jr. | G06K 7/10009 |
| 2018/0077546 | A1 | 3/2018 | Arunachalam et al. | |
| 2018/0118166 | A1* | 5/2018 | Mueller | B60R 25/40 |
| 2018/0293873 | A1* | 10/2018 | Liu | G06K 7/10366 |
| 2018/0338709 | A1* | 11/2018 | Krans | A61B 5/0022 |
| 2018/0357886 | A1* | 12/2018 | Tavori | G08B 21/245 |
| 2019/0079176 | A1* | 3/2019 | Weissman | G01S 3/18 |
| 2019/0180065 | A1* | 6/2019 | Babakhani | A61B 5/0205 |
| 2019/0362304 | A1* | 11/2019 | Suarez | G06Q 10/0833 |

OTHER PUBLICATIONS

Chunli et al., Application and development of RFID technique (Year: 2012).*
Meydanci et al., RFID based hand hygiene compliance monitoring station (Year: 2013).*
Guo et al., The Internet of Things in Extreme Environments Using Low-Power Long-Range Near Field Communication (Year: 2021).*
Thilak et al., Near field magnetic induction Communication in Body Area Network (Year: 2012).*
Rajeev Bansal, Near-field magnetic communication (Year: 2004).*
International Search Report and Written Opinion for International Application No. PCT/US2019/014370, dated Jul. 1, 2019, 20 pages.
Search Report for International Application No. PCT/US2017/058813, dated Feb. 26, 2018.

* cited by examiner

HAND HYGIENE AND SURGICAL SCRUB SYSTEM

CROSS-REFERENCE TO RELATED PATENT APPLICATIONS

This application claims the benefit of and priority to U.S. Provisional Patent Application No. 62/619,549 filed Jan. 19, 2018, and U.S. Provisional Patent Application No. 62/625,223 filed Feb. 1, 2018. Both are incorporated by reference herein in their entireties.

BACKGROUND

The present disclosure relates generally to methods and systems for monitoring and improving hand hygiene. Hand hygiene is an important, and sometimes overlooked, aspect of many environments and occupations. For example, hand hygiene is a critical component of the daily routine of health care workers (HCWs), restaurant/food preparation/food processing workers, and the like. For example, one of the main routes for transmission of infections between patients is improper hand hygiene by HCWs. While workers may be conscious and diligent in their hand sanitization routines, recent studies have shown that HCWs were generally only washed twenty-five percent of the recommended times.

Many hospitals, clinics, restaurants, and food processing plants have implemented various strategies to encourage proper hand-washing/sanitizing, as well as various processes to ensure compliance among employees/workers. For example, many hospitals or other health care facilities have implemented the World Health Organization's (WHO) "Hand Hygiene Guidelines in Health Care" that describe best practices for hand-washing and other hygiene events. Improved systems and methods for ensuring compliance with these best practices would therefore be useful.

SUMMARY

One implementation of the present disclosure is a hand hygiene monitoring system. The system includes a wearable tag device coupled to a user and a reader device communicably coupled to the wearable tag device. The reader device is configured to detect a presence of the wearable tag device by receiving a first frequency message including a user identifier from the wearable tag device. The reader device is further configured to transmit a second frequency message to the wearable tag device requesting event log data. The second frequency has a higher frequency than the first frequency. The reader device is further configured to receive an event log data message from the wearable tag device at the second frequency, and to determine whether the wearable tag device has logged a wash station encounter within a configurable time period based on the event log data message.

In some embodiments, the wearable tag device and the reader device are communicably coupled through near field magnetic induction communications.

In some embodiments, the first frequency is in a range from 30 KHz to 10 MHz. In some embodiments, the second frequency is in a range from 1.9 GHz to 2.1 GHz.

In some embodiments, the reader device is coupled to a threshold of at least one of a patient room, a bathroom, or a kitchen. In other embodiments, the reader device is a flexible mat located proximate to a patient bed.

In some embodiments, the reader device is further configured to transmit a detection message at the first frequency.

In some embodiments, the reader device is further configured to store an encounter success event in a reader event log in response to a determination that the wearable tag device has logged a wash station encounter within the configurable time period. In other embodiments, the reader device is further configured to transmit the encounter success event in the reader event log to a cloud server using cellular communications.

Another implementation of the present disclosure is a method of monitoring hand hygiene. The method includes detecting a presence of a wearable tag device coupled to a user by receiving a first frequency message including a user identifier from the wearable tag device. The method further includes transmitting a second frequency message to the wearable tag device requesting event log data stored in a memory device of the wearable tag device. The second frequency has a higher frequency than the first frequency. The method further includes receiving an event log data message from the wearable tag device at the second frequency, and determining whether the wearable tag device has logged a wash station encounter within a configurable time period based on the event log data message.

In some embodiments, the method includes transmitting a detection message at the first frequency. In some embodiments, the first frequency is in a range from 30 KHz to 10 MHz.

In some embodiments, the method includes storing an encounter success event in a reader event log in response to a determination that the wearable tag device has logged a wash station encounter within the configurable time period. In other embodiments, the method includes transmitting the encounter success event in the reader event log to a cloud server using cellular communications.

Yet another implementation of the present disclosure is hand hygiene monitoring system for a surgical setting. The system includes a wearable tag device coupled to a user, and a reader device communicably coupled to the wearable tag device. The reader device is configured to detect a presence of the wearable tag device by receiving a first frequency message including a user identifier from the wearable tag device. The reader device is further configured to transmit a second frequency message to the wearable tag device requesting user identification data stored in a memory device of the wearable tag device. The second frequency has a higher frequency than the first frequency. The reader device is further configured to detect hand movements of the user during a hand hygiene operation using at least one infrared movement detector, and to determine a real-time compliance status of the hand hygiene operation based on the detected hand movements.

In some embodiments, the reader device is coupled to a scrub station of a surgical scrub sink. In some embodiments, the reader device is coupled to a hand sanitizer dispenser.

In some embodiments, the reader device includes a feedback display configured to display a best practice hand movement of the hand hygiene operation. In other embodiments, the feedback display is configured to display the detected hand movements of the user.

In some embodiments, the first frequency ranges from 30 KHz to 10 MHz. In some embodiments, the second frequency ranges from 1.9 GHz to 2.1 GHz.

In some embodiments, the reader device is further configured to detect a duration of the hand hygiene operation based on the detected hand movements. In other embodiments, the reader device is further configured to determine a real-time compliance status of the hand hygiene operation based on the duration of the hand hygiene operation.

Yet another implementation of the present disclosure is a hand hygiene monitoring system including a reader device. The reader device includes an array of infrared movement detectors and a machine intelligence library. The reader device is configured to detect hand movements of a user during a hand hygiene operation using the array of infrared movement detectors and to utilize machine learning to build and train a stored model of compliant hand hygiene movements in the machine intelligence library.

DETAILED DESCRIPTION

Embodiments described herein provide a method and system for hand hygiene monitoring. According to one aspect, a hand hygiene monitoring system includes tag and reader devices configured to wirelessly communicate with each other. The tag devices may be worn by users (e.g., a healthcare worker (HCW)) in a variety of embodiments, including as a component of a lanyard or wristband, or attached to an ID badge by an adhesive backing, clip, or other fastener. The readers may be small (e.g., approximately 5 inches by 7 inches) battery-operated devices with adhesive backings. A first set of readers may be positioned at the threshold of a room and may be configured to detect a presence of a tag device within a room for a configurable minimum period of time. A second set of readers in the form flexible mat devices may be positioned underneath patient beds to detect the proximity of a tag device to a patient for a configurable minimum period of time. A third set of readers may be positioned near a hand washing station and may be configured to monitor hand hygiene operations. A hand hygiene operation includes, for example, a handwashing event with soap or a handwashing event with alcohol-based hand sanitizer.

Figure 1:
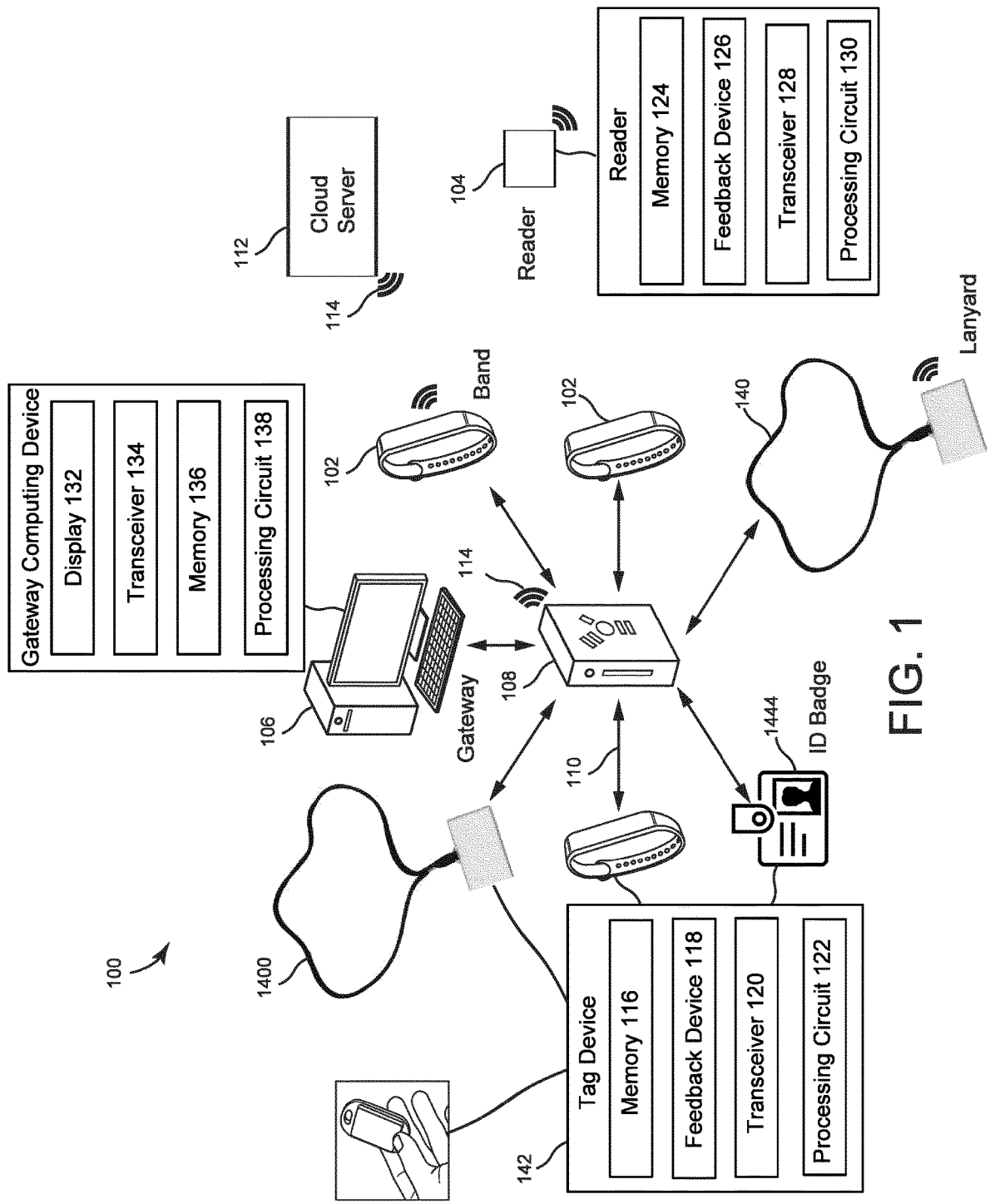
FIG. 1 is a schematic diagram of a hand hygiene system, according to some embodiments.

Referring now to FIG. 1 a schematic diagram of a hand hygiene monitoring or compliance system 100 is depicted, according to some embodiments. Hand hygiene monitoring system 100 includes, among other components, at least one tag device 142 enclosed within or attached to a wristband 102, a lanyard 140, an ID badge holder 144, or otherwise physically associated with the user (e.g., attached to or integrated with a user's phone, or other device). Hand hygiene monitoring system 100 further includes at least one tag reader 104, and a gateway system comprising a gateway computing device 106 and a central hub 108. The tag device 142 enclosed within the wristband 102 or attached to the lanyard 140 or ID badge holder 144 is shown to include, among other components, memory 116, a feedback device 118, a transceiver 120, and a processing circuit 122 in some embodiments. The memory 116 may be configured to store a unique ID number associated with the user, a battery level of the tag device 142, and an event log associated with the user comprising the locations and timestamps of compliant or non-compliant hand washing events. The feedback device 118 may include audible or visual indicators or components (e.g., a speaker, an LED) to indicate compliant or non-compliant hand sanitizing events.

In some embodiments, the transceiver 120 may include three transceiver components oriented orthogonally to each other in an X-Y-Z orientation. This arrangement of transceiver components may form a magnetic flux antenna that can receive signals generated by the tag reader 104 from any direction, Each transceiver component may include one or more receive coils and one or more transmit coils configured to receive and transmit low-frequency (100 KHz-300 KHz) non-propagating magnetic energy using near field magnetic induction (NFMI) communication techniques. The use of low-frequency fields may permit the system to operate on a volumetric basis (i.e., the tag devices and tag readers begin communicating once the tag device enters a space that the tag reader is interrogating) rather than line-of-sight. The dimensions of the volume interrogated by the tag reader are highly configurable (i.e., the tag devices and tag readers can be configured to communicate at distances from a few inches up to 15 feet), and can operate through metals and liquids. In some embodiments, the transceiver 120 further includes one or more receive coils and one or more transmit coils configured to receive and transmit high-frequency (1.5 GHz-2.5 GHz) radio signals. The processing circuit 122 may be configured to process signals received from the transceiver 120. In some embodiments, the processing circuit 122 further includes a timer component, described in further detail with respect to FIGS. 4-5 below. Advantageously, NFMI techniques allow more precise ranges and zones to be set than other radio frequency techniques and are also less susceptible to performance variations due to different body sizes or equipment in the environment.

In various embodiments, the tag reader 104 may be an adhesive-backed, battery operated device affixed near the thresholds of rooms (e.g., a patient room, a bathroom, a kitchen), and on wash stations. In other embodiments, the tag reader 104 may be a flexible mat (e.g., approximately 12 inches by 12 inches) that can be positioned under a patient's bed. Similar to the tag device described above, the tag reader 104 may comprise, among other components, memory 124, a feedback device 126, a transceiver 128, and a processing circuit 130. In further embodiments, the tag reader may have other suitable configurations. The use of NFMI techniques allows the zone around the bed to be defines more precisely and allows the zone to be unaffected by the size of the patient in some embodiments.

The tag reader 104 may also be integrated with a dispensing mechanism of a soap or sanitizer dispenser. For example, the tag reader 104 may be configured to detect the presence of a user wearing a tag device 142, detect a dispensing event, and record the dispensing event in an event log stored in memory 124. In some embodiments, the tag reader 104 may be further configured to detect and record a dispensing malfunction. For example, if the tag reader 104 detects the presence of a user wearing a tag device 142 but does not detect a dispensing event within a configurable time period (e.g., due to a dispenser malfunction or a need to refill the soap or sanitizer stored in the dispenser), the tag reader may store a dispenser malfunction event in the event log.

The wristbands 102, the lanyards 140, and the ID badge holders 144 may connect to the gateway system via a communications interface 110. In some embodiments, communications interface 110 is a universal serial bus (USB) interface. In other embodiments, the wristbands 102, the lanyards 140, and the ID badge holders 144 do not connect to the gateway system directly, and all data collected and/or stored by the tag devices 142 is communicated to the gateway system through the tag reader 104. The gateway computing device processing circuit 138 may process the contents of the memory 136 received from the tag devices and/or the tag reader 104 and display the processed contents via a display 132, such as a video monitor, or may transmit the processed contents to another computing device (e.g., cloud server 112) for analysis and presentation to hygiene monitoring personnel.

Hand hygiene monitoring system 100 is also shown to include a cloud server 112. The cloud server 112 may be configured to store and process data logged by the tag devices 142 and the tag readers 104. For example, in some embodiments, the cloud server 112 may be configured to automatically generate handwashing compliance reports. The cloud server 112 may communicate with the gateway system, the tag devices 142, or the readers 104 via communications interface 114. In various embodiments, communications interface 114 is a long range low power (LoRa) or WiFi network. In other embodiments, communications interface 114 is a cellular communication network.

The tag devices 142 and/or readers 104 may be configured to transmit data to the cloud server 112 at various intervals so that the handwashing data is largely stored and accessible at a server level, as opposed to a tag or reader level. The tag devices 142 and readers 104 may be optimized to transfer data to the cloud server 112 with minimal energy consumption. Further details regarding efficient wireless data transmission processes are disclosed in U.S. patent application Ser. No. 15/618,492, filed Jun. 9, 2017, the entire disclosure of which is incorporated by reference herein.

Figure 2:
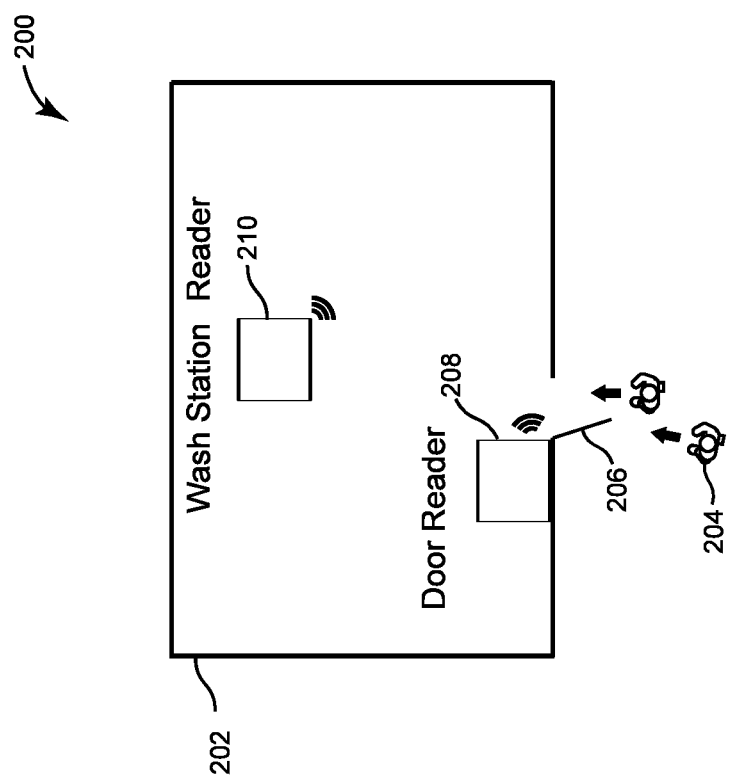
FIG. 2 is a schematic diagram of a user entry reader system utilized in the hand hygiene system of FIG. 1, according to some embodiments.

Referring now to FIG. 2, a schematic diagram of a user entry reader system 200 is shown, according to some embodiments. Door entry reader system 200 may include, among other components, a door reader 208 and a wash station reader 210. The door entry reader system 200 may be implemented in a room 202 (e.g., a patient room, a bathroom, a kitchen) for one or more users 204 (e.g., HCWs) entering the room 202 through a door 206. Each of the users 204 may be wearing a tag device as a component of a lanyard, wristband, or ID badge. The exact location and number of the readers will depend on the layout of the room 202 and the door 206. The layout of the readers may be chosen to achieve the ability to detect the presence of the user within the room 202.

Entry detection occurs when the user 204 (e.g., an HCW) enters the room 202 and the tag device of his or her lanyard, wristband, or ID badge is detected by one or more door readers 208. In some embodiments, the door readers 208 detect the tag device by transmitting a detection signal in a first frequency range of 30 KHz to 10 MHz. In an exemplary embodiment, the first frequency is approximately (i.e., ±15 KHz) 125 KHz. In response, the tag device may transmit a message to the reader 208 at the same frequency. Upon detection of the user's tag device, the door reader 208 may read event log data stored in the memory of the tag device. In some embodiments, the door reader 208 may read event log data by transmitting a request message to the tag device in a second frequency range of 1.9 GHz to 2.1 GHz. In an exemplary embodiment, the second frequency is 2.0 GHz. In response, the tag device may transmit a message containing event log data at the second frequency. Based on the event log data, the reader may alternatively log an entry success event or may begin a configurable timer for the user to encounter a wash station and complete a hand hygiene operation. Further details of this process are included below with reference to FIG. 4.

In some embodiments, the door reader 208 and the wash station reader 210 detect the tag device of user 204 by sensing a signal emitted by the tag device. In other embodiments, the door reader 208 detects the tag device of user 204 by transmitting a signal and receiving a signal from the tag device in response to the transmitted signal. The tag device of the user 204 and the readers 208 and 210 may communicate using any suitable communications method. For example, in some embodiments, the tag devices and readers communicate using NFMI techniques (e.g., transmitter coils on readers may inductively couple with receiver coils on tag devices to pass location data from the readers to the tag devices).

Figure 3:
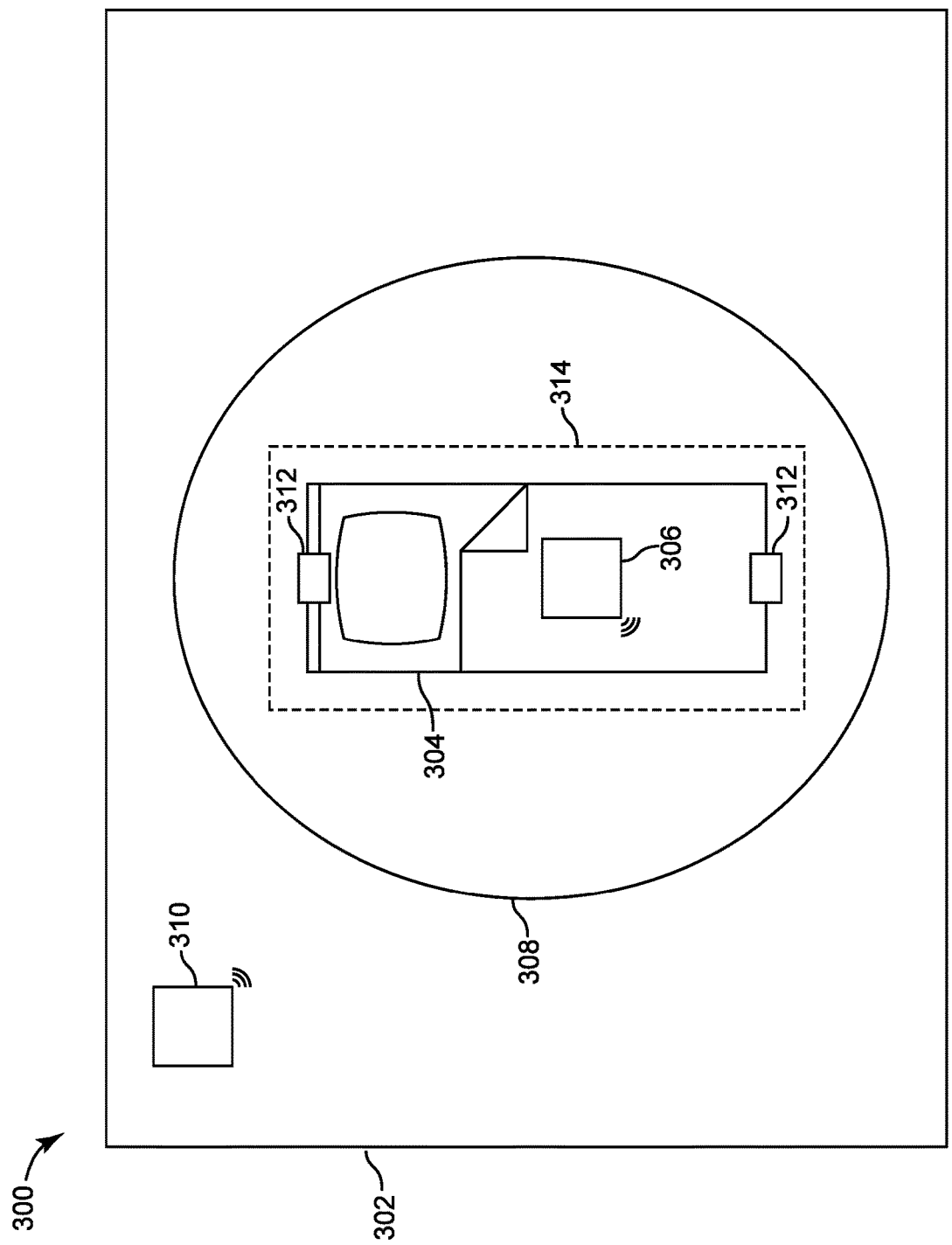
FIG. 3 is a schematic diagram of a patient proximity reader system utilized in the hand hygiene system of FIG. 1, according to some embodiments.

Turning now to FIG. 3, a schematic diagram of a patient proximity reader system 300 is shown, according to some embodiments. Patient proximity reader system 300 may include, among other components, a flexible mat tag reader 306 and a wash station reader 310. As described above, the flexible mat tag reader 306 may be positioned under a patient bed 304 within a patient room 302 and may include a transceiver configured to define a configurable "bubble" or threshold 308 surrounding the patient bed 304. The size of the threshold 308 may be configurable based on the characteristics of the patient, the size of the patient bed 304, or any other characteristic. For example, the threshold 308 surrounding an infant patient may be smaller than the threshold 308 surrounding an adult patient. In some embodiments, the threshold distance may be dependent on the communication method (e.g., NFMI) utilized between the tag devices and the readers. In other embodiments, instead of a flexible mat tag reader 306, multiple repeater antennae 312 may be positioned on or about the patient bed 304. The series of repeater antennae 312 may create a tighter threshold 314 surrounding the patient bed 304.

Patient proximity detection occurs when a user enters the room 302 and approaches the patient bed 304. The tag device of his or her lanyard, ID badge, or wristband may be detected by the flexible mat reader 306 once the user crosses the configurable threshold 308 or 314. Upon detection of the user's tag device, the mat reader 306 may read event log data stored in the memory of the tag device. Based on the event log data, the reader may alternatively log a patient proximity success event or failure event. Further details of this process are included below with reference to FIG. 4.

Figure 4:
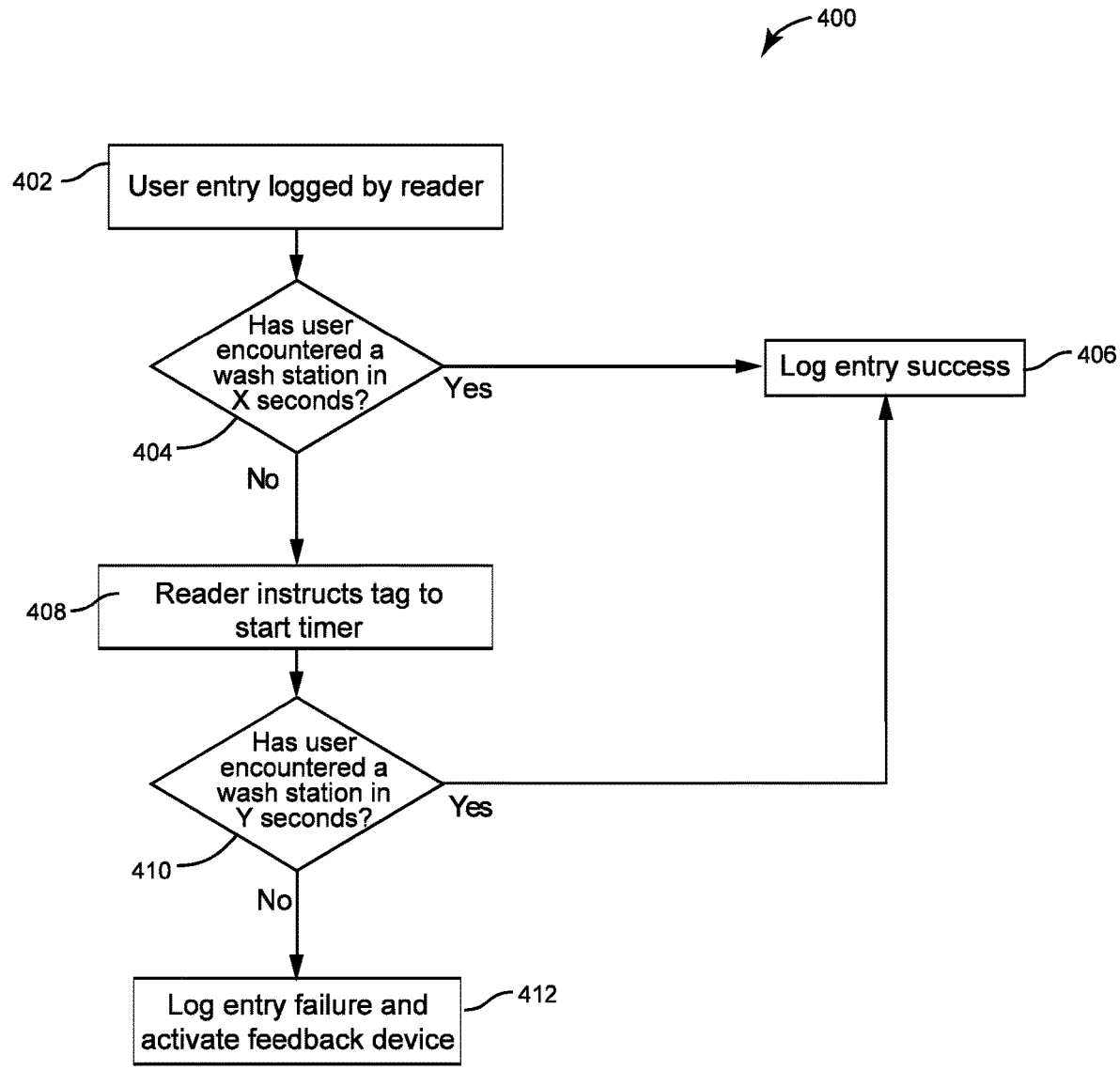
FIG. 4 is a flow diagram of a method for monitoring a user entry, according to some embodiments.

Referring now to FIG. 4, a flow diagram of a process 400 for monitoring a user entry into a room where hand washing facilities are provided (e.g., a patient room, a bathroom, a kitchen) is shown. In some embodiments, the process is performed by one or more components of hand hygiene system 100, described above with reference to FIG. 1. Specifically, process 400 may be performed by a tag device 142 of wristband 102, lanyard 140, or ID badge holder 144, and a reader 104. Process 400 begins at step 402, as a reader 104 detects and logs the entry of a user wearing a tag device 142. The reader 104 may detect the presence of a tag device 142 by transmitting a detection signal in a first frequency range and receiving a message from the tag device 142 in response in the same first frequency range. The message received from the tag device 142 may be a "key" comprising a user identifier (e.g., a user ID number). In some embodiments, the first frequency ranges from 300 KHz to 10 MHz. In an exemplary embodiment, the first frequency is approximately (i.e., ±15 KHz) 125 KHz.

At step 404, the reader determines whether the user wearing the tag device has encountered a wash station within a configurable period of time (e.g., 90 seconds). In some embodiments, the reader 104 determines whether the tag device 142 has encountered the wash station by transmitting a query message in a second frequency range requesting event log data stored in the memory of the tag device 142 and receiving a message from the tag device 142 in response in the same second frequency range. In some embodiments, the second frequency ranges from 1.9 GHz to 2.1 GHz. In an exemplary embodiment, the second frequency is 2.0 GHz. The size of the event log data transmitted between the tag device and the reader may be approximately 10 KB-20 KB. If the reader determines that the user has encountered a wash station within the configurable period of time (e.g., by reading an event log stored in the tag device memory), process 400 advances to step 406, in which the reader records an entry success event in an event log. In various embodiments, the event log may be stored in the memory of one or both of the tag device 142 and the tag reader 104. In some embodiments, the reader 104 records the timestamp and location of the entry success event in an event log associated with the user's unique ID number. At pre-determined intervals, the reader may use a suitable communication network (e.g., LoRa, WiFi) to push the data to a gateway computing device (e.g., gateway computing device 106) that subsequently pushes the event log data to a cloud server (e.g., cloud server 112). In other embodiments, the reader uploads the event log data to the cloud server directly via a cellular communication link.

Returning to step 404, if the reader 104 determines that the user has not encountered a wash station within the configurable period of time, the reader 104 instructs the tag device 142 to begin a timer. In some embodiments, the timer is contained within the processing circuit 122 of the tag device 142. In other embodiments, the timer is contained within the processing circuit 130 of the reader device 104. Continuing with step 410, the reader determines whether the user wearing the tag device 142 has encountered a wash station within a second configurable time period (e.g., 15 seconds). If the reader 104 determines that the user has encountered a wash station within the second configurable time period, process 400 advances and concludes at step 406, in which the reader records an entry success event in an event log. If, however, the reader determines that the user has not encountered a wash station within the second configurable time period, process 400 concludes at step 412 by recording an entry failure event in an event log. In some embodiments, step 412 also includes providing the user with feedback (e.g., an alarm sound, a flashing light) by activating a feedback device (e.g., feedback device 118).

Figure 5:
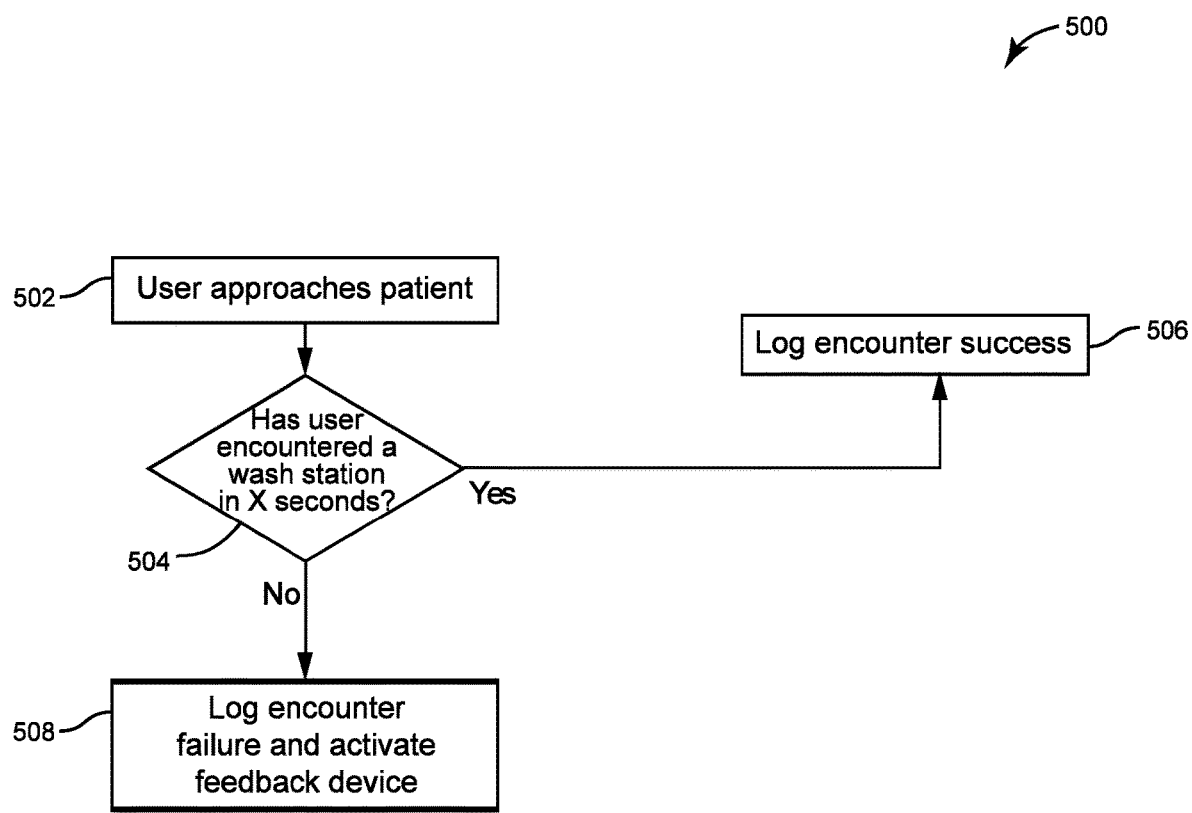
FIG. 5 is a flow diagram of a method for monitoring a patient encounter, according to some embodiments.

Referring now to FIG. 5, a process 500 for monitoring a patient encounter is shown, according to some embodiments. In some embodiments, the process is performed by one or more components of hand hygiene system 100, described above with reference to FIG. 1. Specifically, process 500 may be performed by a tag device 142 of wristband 102, lanyard 140, or ID badge 144, and a reader 104. Process 500 begins at step 502, as a reader 104 detects the presence of the user as the user approaches the patient. In some embodiments, detection of the user presence may occur when the user crosses the configurable "bubble" or threshold surrounding the patient bed. The reader 104 may detect the presence of a tag device 142 by transmitting a detection signal in a first frequency range and receiving a message from the tag device 142 in response in the same first frequency range. The message received from the tag device 142 may be a "key" comprising a user identifier (e.g., a user ID number). In some embodiments, the first frequency ranges from 30 KHz to 10 MHz. In an exemplary embodiment, the first frequency is approximately (i.e., ±15 KHz) 125 KHz. The use of the key allows communication in the second frequency range to be directed for device to device communication without unnecessarily interfering with other devices communicating in the high frequency range in some embodiments.

At step 504, the reader determines whether the user wearing the tag device 142 has encountered a wash station within a configurable period of time (e.g., 90 seconds). In some embodiments, the reader 104 determines whether the tag device 142 has encountered the wash station by transmitting a query message in a second frequency range requesting event log data stored in the memory of the tag device 142 and receiving a message from the tag device 142 in response in the same second frequency range. In some embodiments, the second frequency ranges from 1.9 GHz to 2.1 GHz. In an exemplary embodiment, the second frequency is 2.0 GHz. The size of the event log data transmitted between the tag device and the reader may be approximately 10 KB-20 KB. If the reader 104 determines that the user has encountered a wash station within the configurable period of time (e.g., by reading an event log stored in the tag device memory), process 500 advances to step 506, in which the reader 104 records an encounter success event in an event log. In various embodiments, the event log may be stored in the memory of one or both of the tag device 142 and the tag reader 104. In some embodiments, the reader 104 records the timestamp and location of the encounter success event in an event log associated with the user's unique ID number. At pre-determined intervals, the reader 104 may use a suitable communication network (e.g., LoRa, WiFi) to push the data to a gateway computing device (e.g., gateway computing device 106) that subsequently pushes the event log data to a cloud server (e.g., cloud server 112). In other embodiments, the reader 104 uploads the event log data to the cloud server 112 directly via a cellular communication link.

If, however, the reader 104 determines at step 504 that the user has not encountered a wash station within the second configurable time period, process 500 concludes at step 508 as the reader 104 records an encounter failure event in an event log. In some embodiments, step 508 also includes providing the user with feedback (e.g., an alarm sound, a flashing light) by activating a feedback device (e.g., feedback device 118).

Figure 6:
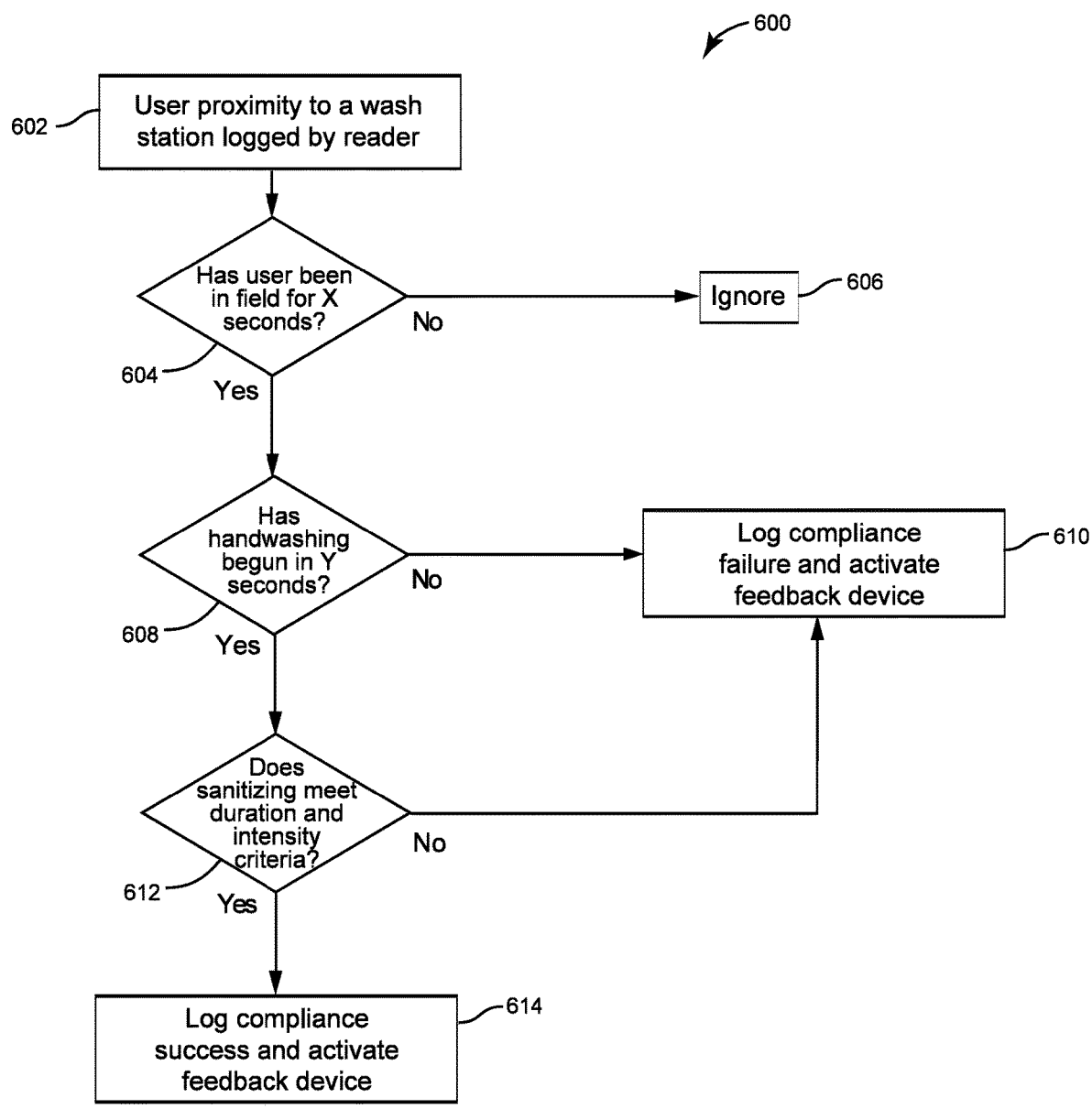
FIG. 6 is a flow diagram of a method for monitoring wash station encounters, according to some embodiments.

Turning now to FIG. 6, a process 600 for monitoring wash station access is shown, according to some embodiments. Process 600 may be performed by one or more components of hand hygiene system 100, described above with reference to FIG. 1. Specifically, process 600 may be performed by a wristband 102, lanyard 140, or ID badge 144 containing a tag device 142 and one or more tag readers 104. In various embodiments, the wash station (e.g., a soap dispenser, a hand sanitizer dispenser) is located in a patient room (e.g., room 202 or room 302, described above with reference to FIGS. 2-3), a bathroom, or a kitchen.

Beginning at step 602, the wash station tag reader (e.g., wash station reader 210, wash station reader 310) detects that the user wearing the tag device 142 is within a configurable distance (e.g., 1 foot) of the tag reader and logs the presence of the tag device 142 by transmitting and receiving a signal (e.g., a key message) at a first frequency (e.g., 125 KHz). As described above, in some embodiments, logging the presence of the tag device includes requesting, receiving, and storing data related to the tag device 142, including, but not limited to, a unique ID number associated with the user wearing the tag device 142, a timestamp of the tag device detection, and a battery level of the tag device 142. In some embodiments, the data related to the tag device 142 is transmitted to the reader at a second frequency (e.g., 2.0 GHz).

At step 604, the wash station reader determines whether the user wearing the tag device 142 has been within the configurable distance of the tag reader 104 for a minimum configurable period of time (e.g., 2 seconds). If the reader 104 determines that the user wearing the tag device 142 has not been within the configurable distance of the reader 104 for the minimum period of time (e.g., if the user merely walks past the wash station reader and does not stop near the wash station), process 600 advances to step 606 as the reader 104 ignores the presence of the tag device-wearing user. In some embodiments, ignoring the presence of the user may include deleting data related to the user presence from the event log. In other embodiments, ignoring the presence of the user may include recording the ignore event in the event log. If, however, the user has been within the configurable distance of the tag reader 104 in excess of the minimum configurable period of time, process 600 advances to step 608.

At step 608, the tag reader 104 detects whether the user has begun a hand sanitizing event within a second configurable period of time (e.g., 2.5 seconds). The tag reader 104 may detect whether the hand sanitizing event has commenced using a variety of methods. In some embodiments, the tag reader 104 may be configured to emit a radio field, and movements of a wrist-worn tag device 142 may result in power level changes to the radio field that can be detected by the reader unit 104. In still further embodiments, the presence of a tag device 142 worn by the user is not required to detect a handwashing event. For example, the reader 104 may be configured to detect patterns of radio reflections caused by handwashing motions using micro Doppler radar techniques. As another example, the wash station may include an infrared sensor array of infrared emitters and infrared receivers configured as movement detectors, and the reader may be configured to detect signals passed as digital magnitude counts. The emitters and receivers can operate in the near infrared band or other band in some embodiments. In some embodiments, a single emitter is provided with an array or receivers or a signal receivers provided with an array of emitters.

If the reader 104 determines that hand sanitizing has not commenced within the second configurable period of time, process 600 advances to step 610, and the reader 104 logs a compliance failure. In some embodiments, the reader 104 records the timestamp and location of the wash failure in an event log associated with the user's unique ID number. At pre-determined intervals, the reader 104 may use a suitable communication network (e.g., LoRa, WiFi) to push the data to a gateway computing device (e.g., gateway computing device 106) that subsequently pushes the event log data to a cloud server (e.g., cloud server 112). In other embodiments, the reader 104 uploads the event log data to the cloud server 112 directly via a cellular communication link. In addition, the tag device 142 worn by the user and/or the reader 104 may signal the wash failure through an audible and/or visible feedback signal to the user (e.g., emitting a failure noise, flashing a red LED). If, however, the reader determines that handwashing has commenced within the second configurable period of time, process 600 advances to step 612.

At step 612, the reader determines whether the hand sanitizing movements detected in step 608 meet movement duration and intensity criteria. These criteria are configurable, and may be dependent upon the type of wash station (i.e., the criteria for a successful wash event utilizing soap may differ from the criteria for a successful wash event utilizing hand sanitizer). In some embodiments, a machine intelligence algorithm applied either directly or indirectly by the tag reader 104 may be utilized to determine whether the handwashing movements satisfy the duration and intensity criteria. If the reader 104 determines that the handwashing movements do not meet duration and intensity criteria, process 600 may revert and conclude at step 610 by the reader 104 logging a wash failure. If, however, the reader 104 determines that the handwashing movements meet movement duration and intensity criteria, process 600 may conclude at step 614 with the reader 104 logging a compliance success. In some embodiments, the handwashing movement criteria may be based on the hand movements of the WHO's six step hand hygiene protocol, described in further detail below with reference to FIG. 10. In addition to logging the compliance success, the tag device 142 worn by the user and/or the reader may signal the wash success through an audible and/or visible feedback signal to the user (e.g., emitting a success noise, flashing a green LED).

Further embodiments described herein provide a method and system for hand hygiene monitoring in a surgical setting. According to one aspect, the system includes tag and reader devices configured to wirelessly communicate with each other. The tag devices may be worn by users in a variety of embodiments, including as a component of a lanyard or attached to an ID badge by an adhesive backing. The reader devices may be installed near scrub faucets and hand sanitizer dispensers to detect the presence of a user wearing a tag device. The reader device may also be configured to monitor and provide real-time feedback to a user regarding the compliant or non-compliant status of a surgical scrub hand hygiene operation using a variety of methods. A surgical scrub hand hygiene operation may include, for example, a handwashing event with soap, use of a nail brush or nail pick, and a handwashing event with alcohol-based hand sanitizer.

Figure 7:
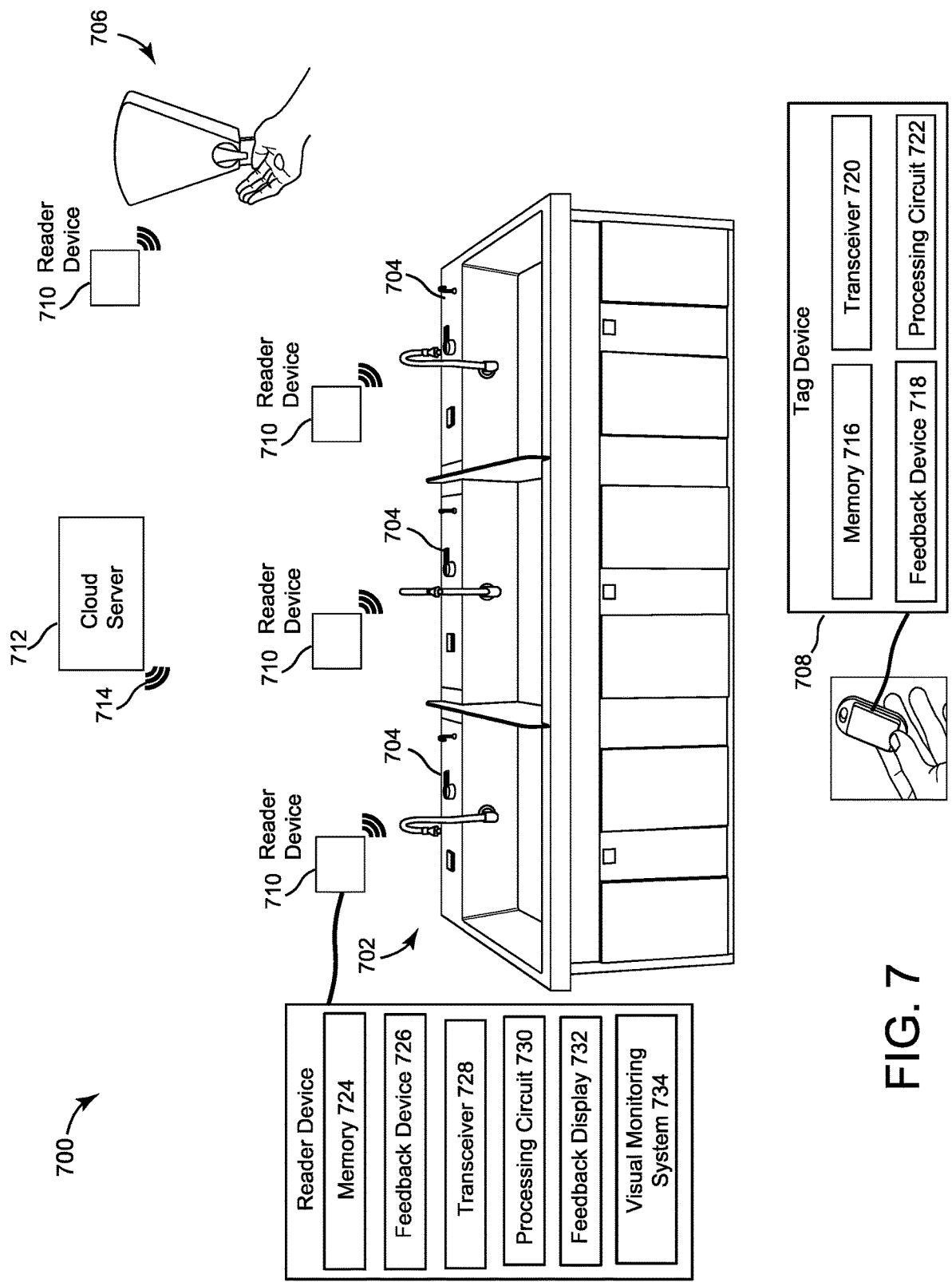
FIG. 7 is a schematic diagram of a surgical scrub hand hygiene system, according to some embodiments.
Figure 8:
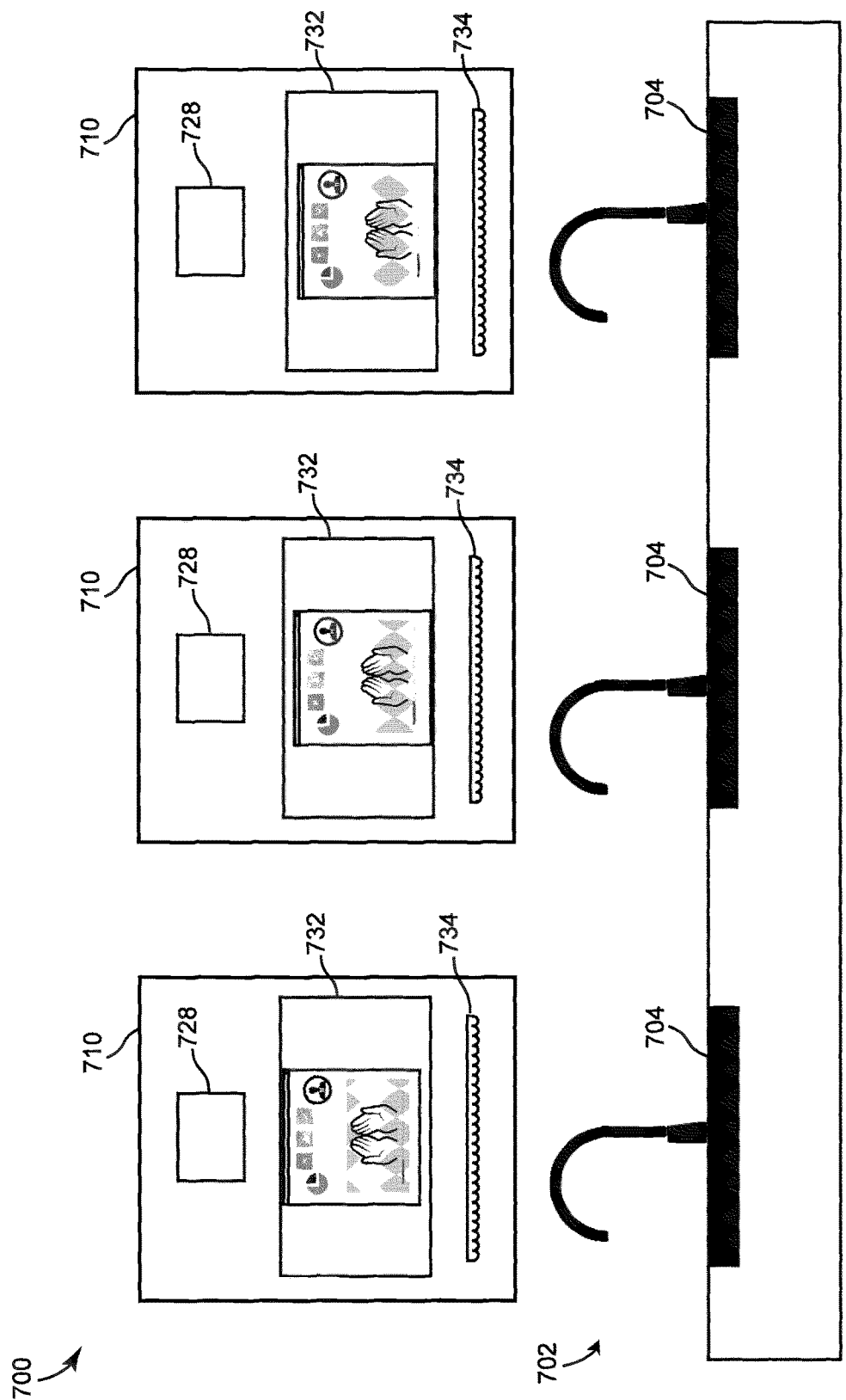
FIG. 8 is another schematic diagram of the surgical scrub hand hygiene system of FIG. 7, according to some embodiments.

Referring now to FIGS. 7 and 8, schematic diagrams of a surgical scrub hand hygiene system 700 are shown, according to some embodiments. Surgical scrub hand hygiene system 700 includes, among other components, a multi-station scrub sink 702, a sanitizer dispenser 706, a tag device 708, at least one reader device 710, and a cloud server 712. Multi-station scrub sink 702 is shown to include several scrub stations 704. In various embodiments, each scrub station 704 includes a faucet and a soap dispenser, which may be activated using a variety of hands-free methods (e.g., knee-operated switches, automatic sensors). Each scrub station 704 and sanitizer dispenser 706 is shown to be associated with a dedicated reader device 710 that both detects the presence of a user wearing a tag device 708 and monitors a hand sanitizing operation performed by the user at the scrub station 704 or the sanitizer dispenser 706.

In various embodiments, the tag device 708 may be worn by a user in any suitable fashion (e.g., as a component of a lanyard, affixed to an ID badge). Tag device 708 is shown to include, among other components, memory 716, a feedback device 718, a transceiver 720, and a processing circuit 722. The memory 716 may be configured to store a unique ID number associated with the user, a battery level of the tag device 708, and an event log associated with the user comprising the locations and timestamps of compliant or non-compliant hand sanitizing operations. The feedback device 718 may include audible or visual indicators or components (e.g., a speaker, an LED) to indicate compliant or non-compliant hand sanitizing events. The transceiver 720 is configured to communicably couple the tag device 708 to the reader device 710 and/or the cloud server 712. In some embodiments, the transceiver 720 is a magnetic flux antenna configured to receive and transmit low-frequency (100 KHz-300 KHz) non-propagating magnetic energy using near field magnetic induction (NFMI) communication techniques. In some embodiments, the transceiver 720 further includes one or more receive coils and one or more transmit coils configured to receive and transmit high-frequency (1.5 GH-2.5 GHz) radio signals. The processing circuit 722 may be configured to process signals received from the transceiver 720.

The reader device 710 may be configured to both detect the presence of a user wearing a tag device 708 and to monitor and provide real-time feedback to the user regarding the user's compliance with required surgical scrubbing techniques. In some embodiments, the reader device 710 is battery-operated, in other embodiments the reader device 710 utilizes a hard-wired power connection. The reader device is shown to include, among other components, memory 724, a feedback device 726, a transceiver 728, a processing circuit 730, a feedback display 732, and a visual monitoring system 734. The memory 724 may be configured to store imaging data captured by the visual monitoring system 734, as well as an event log of compliant and non-compliant hand sanitizing operations. The feedback device 726, similar to the feedback device 718 of the tag device 708, may include audible or visual indicators or components (e.g., a speaker, an LED) to indicate compliant or non-compliant hand sanitizing events. The transceiver 728 is configured to communicably couple the reader device 710 to the tag device 708 and/or the cloud server 712 utilizing any suitable communications techniques (e.g., NFMI).

The processing circuit 730 may be configured to utilize imaging data captured by the visual monitoring system 734 to determine whether the hand sanitizing operations performed by the user meet compliance standards. In some embodiments, the processing circuit 730 utilizes visual algorithms to detect the start and end of a hand sanitizing operation, and to compare the imaging data with stored best practice hygiene techniques. The processing circuit 730 may utilize different visual algorithms based on the location of the reader device 710 (e.g., best practice hygiene techniques differ based on whether the user is performing a hand sanitizing operation with soap or alcohol-based hand sanitizer). Deviations from best practices may be communicated to the user through the feedback device 726 and the feedback display 732, as well as through the feedback device 718 of the tag device 708. In some embodiments, the processing circuit 730 may include a visual analysis engine that is configured to recognize hygiene tools utilized by a user during a hand sanitizing operation. For example, the visual analysis engine may be configured to detect tools such as fingernail picks, brushes, and sponges.

Reader device 710 is also shown to include a feedback display 732 and a visual monitoring system 734. In various embodiments, feedback display 732 may be a liquid crystal display (LCD) or any other suitable type of display. Further details regarding the user interface components that may be displayed on feedback display 732 are included below with reference to FIGS. 9 and 10. The visual monitoring system 734 may be configured to capture imaging data of the hand movements of a user performing a hand sanitizing operation. In an exemplary embodiment, the visual monitoring system 734 may utilize multiple infrared emitters and movement detectors, due to their low cost relative to visible light cameras and their ability to capture usable data with fewer pixels than visible light cameras. In other embodiments, the visual monitoring system 734 may include a single visible light camera, or a stereo camera system employing more than one visible light camera. Further details of the visual monitoring system 734 are included below with reference to FIG. 11.

Surgical scrub hand hygiene system 700 is also shown to include a cloud server 712. The cloud server 712 may be configured to store and process data logged by the tag devices 742 and the reader devices 710. For example, this data may include visual data regarding a user's precise hand sanitizing movements to allow incorrect hand movements to be flagged and presented to the user. In some embodiments, the cloud server 712 may be configured to automatically generate hand sanitizing compliance reports for a variety of audiences, including the infection control board of a health care facility. For example, the use of a waterless hand sanitizer (e.g., Avaguard sanitizer manufactured by 3M) may be indicated for use in a surgical setting under limited conditions, for example, emergency surgery conditions when the time required to complete a surgical scrub procedure utilizing soap is not available. Based on imaging data captured by the reader devices 710 and additional data shared with the cloud server 712 (e.g., emergency classifications of surgeries performed by the user), the cloud server 712 may generate reports regarding a user's compliance level regarding the acceptable use of hand sanitizer. The cloud server 712 may communicate with the tag devices 708 and/or the reader devices 710 via communications interface 714. In various embodiments, communications interface 714 is a long range low power (LoRa) or WiFi network. In other embodiments, communications interface 714 is a cellular communication network.

Figure 9:
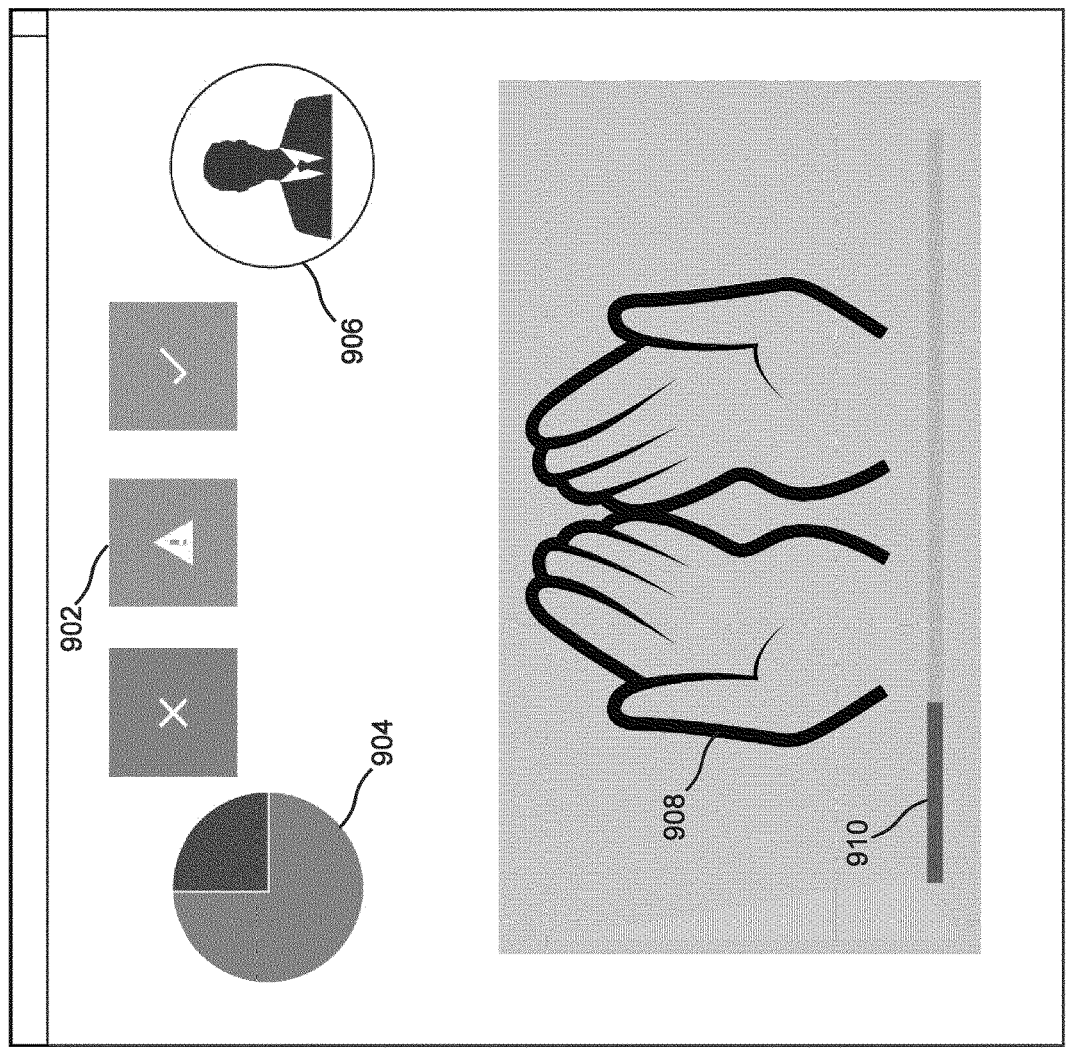
FIG. 9 is a schematic diagram of a feedback display used in the surgical scrub hand hygiene system of FIG. 7, according to some embodiments.

Referring now to FIG. 9, a schematic diagram of a user interface 900 is shown. In various embodiments, the user interface 900 may be displayed on the feedback display 732 of the reader device 710 and may include, among other components, multiple feedback indicators 902, a timer 904, a user profile 906, a hand movement display component 908, and a status bar indicator 910. The feedback indicators 902 may be icons or other user interface components (e.g., a red "X," a green checkmark symbol) that are selectively illuminated or presented to the user based on the compliant or non-compliant status of the hand sanitizing operation. In some embodiments, the feedback indicators 902 may include a caution icon (e.g., a yellow or orange yield symbol) that indicates that the hand sanitizing operation is borderline compliant.

The timer 904 may provide a visual indicator to the user of the time elapsed since the start of the hand sanitizing operation or the time remaining to complete a compliant hand sanitizing operation. Similarly, the status bar indicator 910 may provide a visual indication of how much longer the user must perform a particular step in a hand sanitizing operation (e.g., moving hands in a certain scrubbing pattern, utilizing a fingernail pick, utilizing a scrub brush) in order for that step in the operation to be deemed compliant. The user profile 906 may indicate to the user that the reader device 710 has successfully coupled to the user's tag device 708 and has received user-identifying information (e.g., a user ID number) from the tag device 708. For example, the user profile 906 may display a picture of the user to ensure that captured hand sanitizing data is associated with the correct user.

Figure 10:
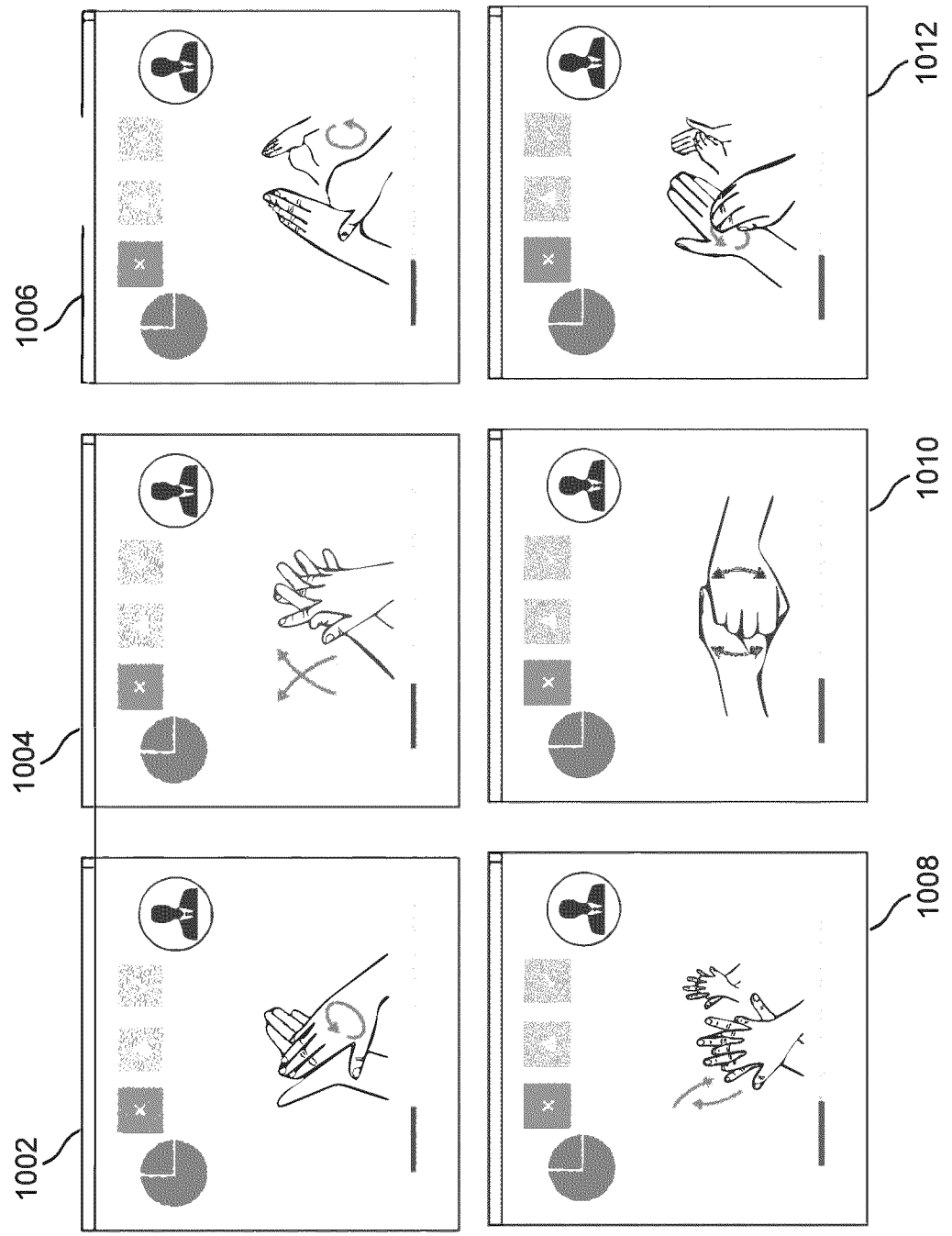
FIG. 10 is a series of schematic diagrams of feedback displays used in the surgical scrub hand hygiene system of FIG. 7, according to some embodiments.

The hand movement display component 908 may display best practice hand movements for a sanitizing operation. Turning now to FIG. 10, a series of schematic diagrams 1002-1012 of the user interface are depicted. As shown, various example hand movements comprising a compliant surgical scrub hand sanitizing operation may be shown on the hand movement display component 908 of the user interface 900 depicted in FIG. 9. For example, each of the schematic diagrams 1002-1012 depicts a specific hand movement of the WHO's six step hand hygiene protocol. The movements include: 1) rubbing hands from palm to palm (depicted in 1002), 2) rubbing palm to palm with fingers interlace (depicted in 1004), 3) rotational rubbing of left thumb clasped in right palm and vice versa (depicted in 1006), 4) rubbing right palm over left backhand with interlaced fingers and vice versa (depicted in 1008), 5) rubbing backs of fingers to opposing palms with fingers interlocked (depicted in 1010), and 6) rotational rubbing, backwards and forwards with clasped fingers of right hand in left palm and vice versa (depicted in 1012).

In some embodiments, the hand movement display 908 may be configured to display imaging data captured by the visual monitoring system (e.g., the infrared movement detectors of the visual monitoring system 734) in a split screen configuration with the best practice hand movements. In further embodiments, the hand movements of the user may be overlaid on best practice movements using augmented reality to demonstrate the user's compliant or non-compliant status.

Figure 11:
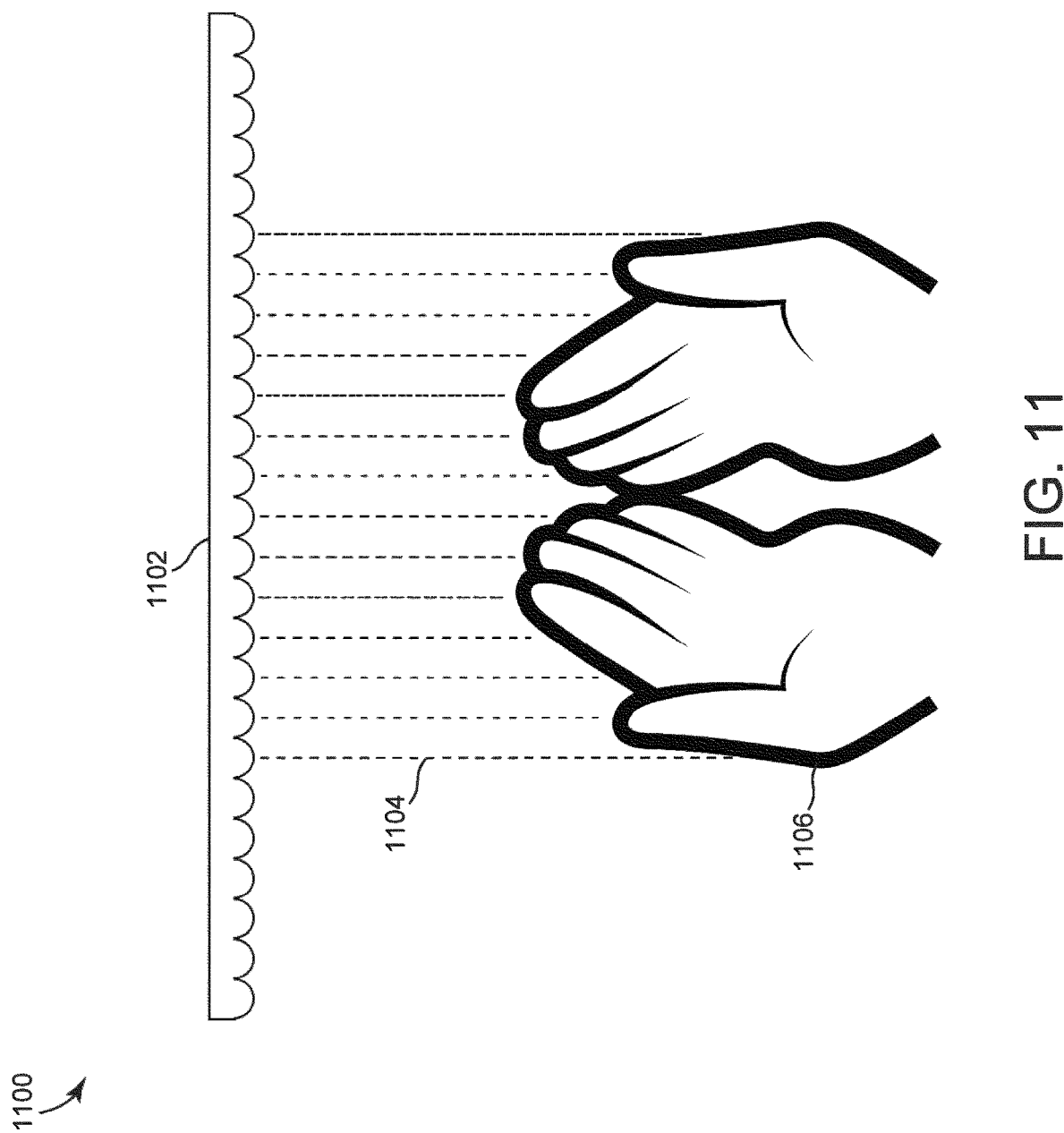
FIG. 11 is a schematic diagram of a visual monitoring system used in the surgical scrub hand hygiene system of FIG. 7, according to some embodiments.

Referring now to FIG. 11, schematic diagram 1100 of a visual monitoring system in operation is shown, according to some embodiments. Diagram 1100 is shown to include a visual monitoring system 1102. In various embodiments, visual monitoring system 1102 is identical or substantially similar to visual monitoring system 734, described above with reference to FIGS. 7 and 8, and includes one or more infrared emitters and movement detectors. Diagram 1100 is also shown to include infrared radiation 1104 emitted by the one or more infrared emitters intersecting a user's hands 1106. The intersections between the radiation 1104 and the user's hand 1106 may be detected by the one or more infrared movement detectors and permit the user's hand movements to be captured, analyzed, and subsequently displayed on the user interface 900 of the feedback display 732.

Figure 12:
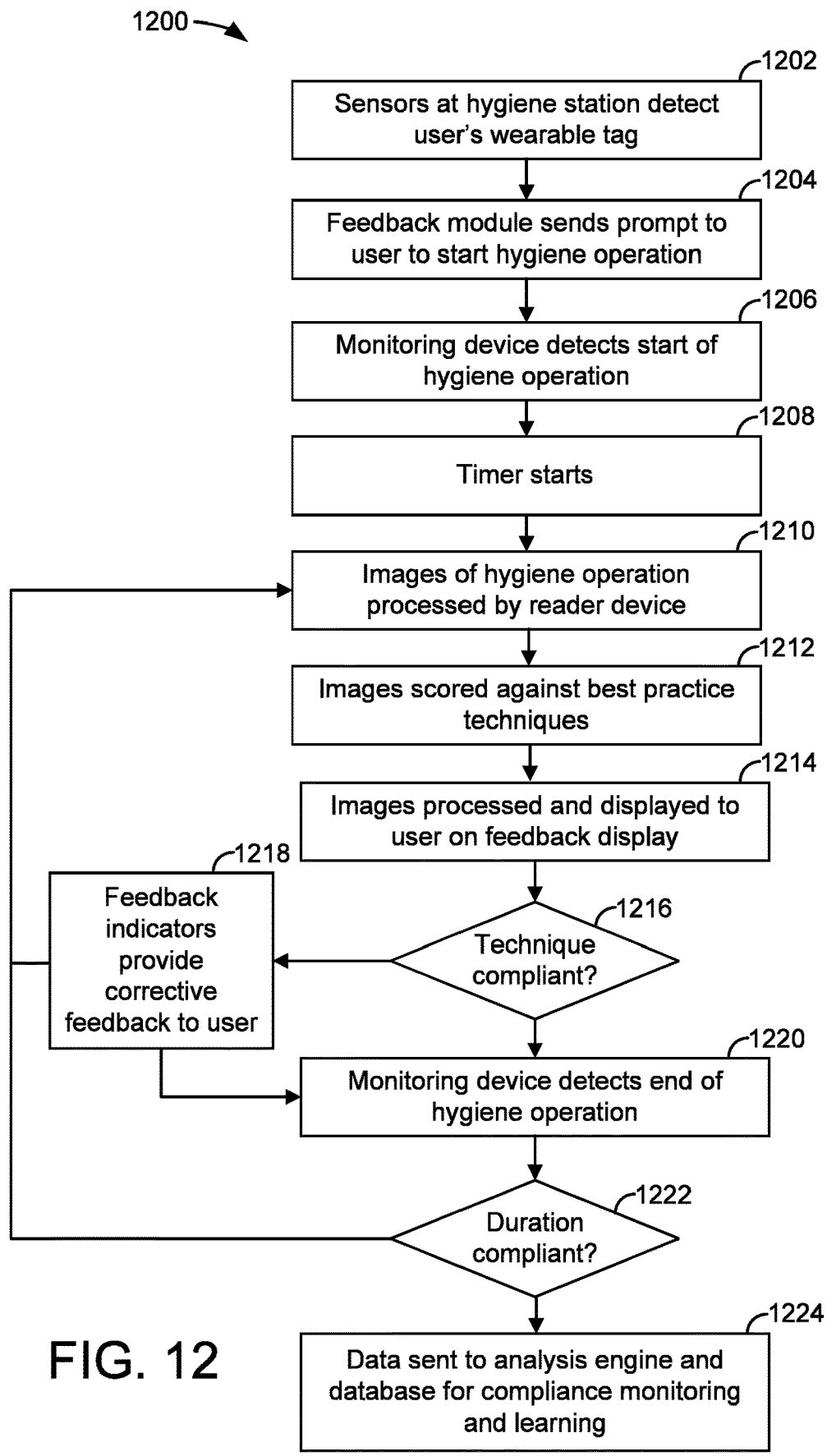
FIG. 12 is a flow diagram of a method for monitoring wash station encounters, according to some embodiments.

Turning to FIG. 12, a process 1200 for monitoring a surgical hand sanitizing operation is shown, according to some embodiments. Process 1200 may be performed by one or more components of the surgical scrub hand hygiene system 700. Process 1200 begins with step 1202, in which sensors at a hygiene station (e.g., a transceiver 728 of a reader device 710) detects the presence of a user's wearable tag (e.g., tag device 708). The reader 710 may detect the presence of a tag device 708 by transmitting a detection signal in a first frequency range and receiving a message from the tag device 708 in response in the same first frequency range. The message received from the tag device 708 may be a "key" comprising a user identifier (e.g., a user ID number). In some embodiments, the first frequency ranges from 30 KHz to 10 MHz. In an exemplary embodiment, the first frequency is approximately (i.e., ±15 KHz) 125 KHz.

At step 1204, a feedback module (e.g., a message displayed on user interface 900 of feedback display 732) prompts the user to begin a hand hygiene operation. In some embodiments, step 1204 includes the reader 710 transmitting a request for user identification and/or user-associated data stored in the tag device 708 and receiving the user data at a second frequency. In some embodiments, the second frequency ranges from 1.9 GHz to 2.1 GHz. In an exemplary embodiment, the second frequency is 2.0 GHz.

Continuing with step 1206, a monitoring device (e.g., the infrared movement detectors of visual monitoring system 734) detects the start of a hygiene operation. At step 1208, a timer is started. In various embodiments, the timer is a component of the processing circuit 730 of the reader device 710, and the elapsed time may be displayed to the user as timer component 904 of user interface 900. At step 1210, imaging data of the hand hygiene operation is captured by a monitoring device (e.g., visual monitoring system 734). Continuing with step 1212, the imaging data is scored against best practice techniques. In some embodiments, the imaging data is scored by the processing circuit 730 using visual algorithms and/or artificial learning techniques. At step 1214, the imaging data is processed and displayed to the user on a feedback display (e.g., hand movement display component 908 of the user interface 900). In some embodiments, the processing circuit 730 is trained by machine learning techniques to identify compliance. The processing circuit 730 can be trained to identify the six hand motions of FIG. 10 for compliance in some embodiments. In some embodiments, the processing circuit 730 is neural network trained using samples of pixel data captured over time showing hand movements. The pixel data can be from infrared sensors (e.g., infrared movement detectors) or visible or other cameras. Various regression analysis, weighting algorithms, and video processing techniques can be used to determine the proper hand motions in pixel data over time.

At step 1216, a processing device (e.g., the processing circuit 730) determines whether the user's hygiene techniques are compliant with best practices. If the processing device determines that the hygiene techniques are not compliant, process 1200 proceeds to step 1218, and feedback indicators provide real-time corrective feedback to the user. As described above, the corrective feedback may be displayed on the user interface 900, or it may be indicated by the feedback device 718 of the user's tag device 708. If, however, the processing device determines that the hygiene techniques are compliant, process 1200 advances to step 1220, in which the monitoring device (e.g., visual monitoring system 734) detects the end of the hand hygiene operation. In some embodiments, detection of the end of the hand hygiene operation is also performed via proximity detection of the tag device 708.

At step 1222, the processing device (e.g., the processing circuit 730) determines whether the duration of the hand hygiene operation complies with best practices. If the processing device determines that the duration is insufficient, process 1200 reverts to steps 1210 and 1218 and provides feedback of the non-compliance, prompting the user to continue the hand hygiene operation. If, however, the processing device determines at step 1222 that the duration of the hand hygiene operation was sufficient, the processing device sends the captured image data to an analysis engine and database (e.g., the cloud server 712) for compliance monitoring and learning. In some embodiments, the analysis engine can use artificial learning techniques to train the visual monitoring system 734 to better detect compliant or non-compliant hand washing movements.

Figure 13:
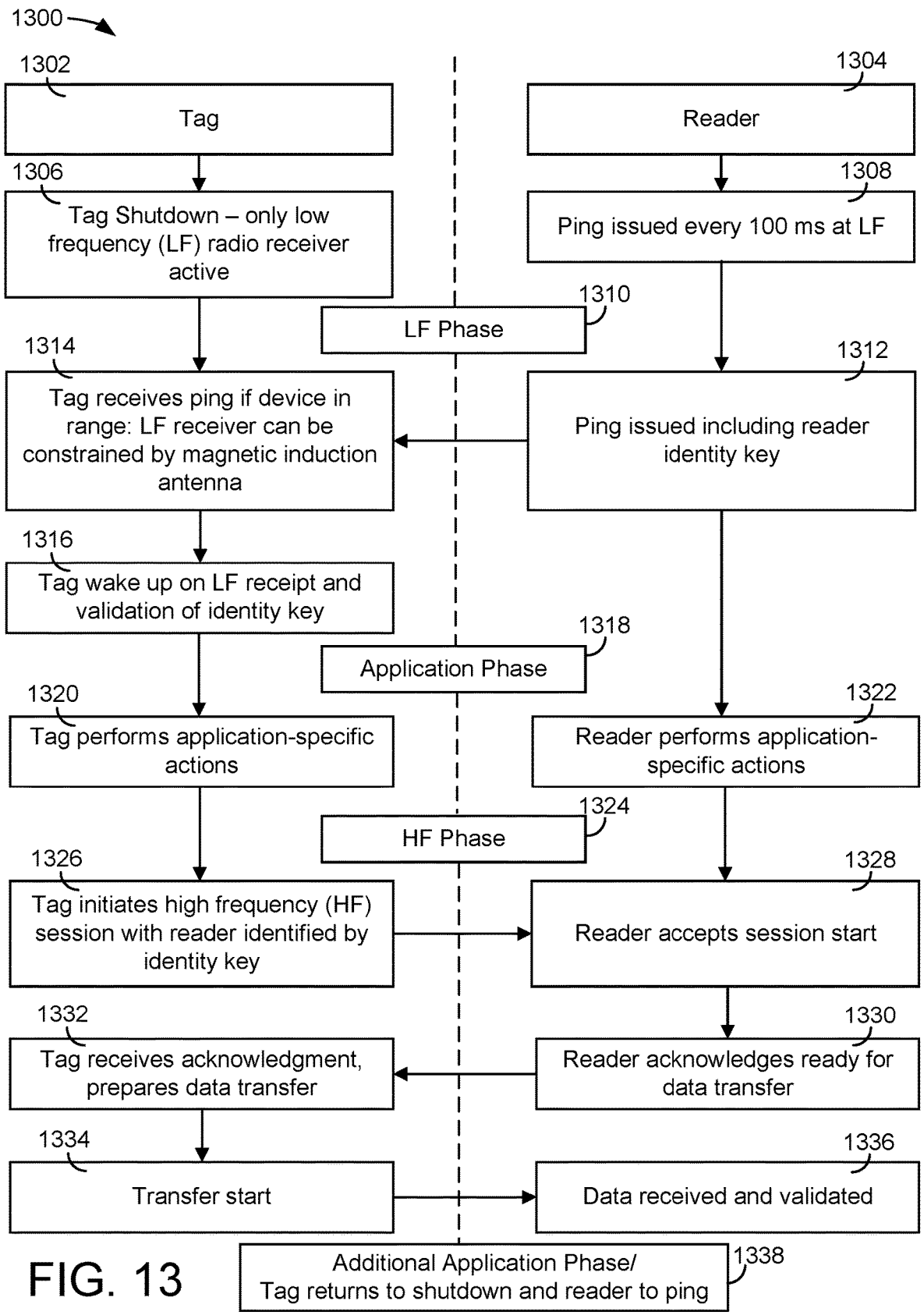
FIG. 13 is a flow diagram of a method for monitoring wash station encounters, according to some embodiments.

Referring now to FIG. 13, a method 1300 for monitoring a hand hygiene operation is shown. The method may be performed by tag 1302 and reader 1304. In some embodiments, tag 1302 is identical or substantially similar to tag 142 or tag 708, as described above. In some embodiments, reader 1304 is identical or substantially similar to reader 104 or reader 710, as described above.

At step 1306, the tag 1302 is operating in a shutdown state. In the shutdown state, only a low frequency (LF) radio receiver may be active. Operating in the shutdown state may act to preserve the battery life of the tag 1302. At step 1308, the reader 1308 issues ping messages every 100 ms at LF. In some embodiments, the LF pings are emitted at a frequency ranging from 30 KHz to 10 MHz. In various embodiments, steps 1306 and 1308 may occur simultaneously.

Beginning at step 1310, the tag 1302 and the reader 1304 operate in a LF phase. At step 1312, the reader 1304 issues a ping including a reader identity key 1312. In various embodiments, the reader identity key can include a serial number of the reader 1304, an installation location of the reader 1304, or any other information used to identify the reader 1304 to the tag 1302. At step 1314, the tag 1302 receives the ping from the reader 1304 if the tag 1302 is within range. In various embodiments, the upper range of the LF receiver on the tag 1302 can be constrained by a magnetic induction (i.e., NFMI) antenna. In other embodiments, the radio receiver of the tag 1302 can also employ a power measurement to refine the range of reception. In still further embodiments, the radio receiver only employs a power measurement to define the range of reception. If the tag 1302 is within the range of the reader 1304, the tag 1302 enters a wake state at step 1316 and performs a validation step of the identity key received from the reader 1304.

Beginning at step 1318, the tag 1302 and the reader 1304 operate in an application phase. At step 1320, the tag 1302 performs application-specific actions. At step 1322, the reader 1304 performs application-specific actions. Application-specific actions may include, but are not limited to, actions such as advancing state machines and storing data. In some embodiments, applications for the tag 1302 and the reader 1304 are stored in the memory of each device. In various embodiments, steps 1320 and 1322 are performed simultaneously.

Beginning at step 1324, the tag 1302 and the reader 1304 operate in a high frequency (HF) phase. Both the tag 1302 and the reader 1304 can include a HF radio receiver. In various embodiments, the HF radio receiver can be a receiver operating at a radio protocol of 1 GHz or above. In an exemplary embodiment, the HF radio receiver is a Bluetooth radio receiver operating at a frequency of approximately 2 GHz in a direct addressing mode. The direct addressing mode affords a short duration data transfer at a very fast speed.

At step 1326, the tag 1302 initiates a HF session with the reader 1304 identified by the identity key received at step 1316. At step 1328, the reader 1304 accepts the start of the HF session. Continuing with step 1330, the reader 1304 transmits a message acknowledging that the reader 1304 is ready for data transfer. At step 1332, the tag 1302 receives the acknowledgement message from the reader 1304 and prepares for data transfer. At step 1334, data transfer begins from the tag 1302 to the reader 1304 using a HF radio protocol. In various embodiments, the data transferred from the tag 1302 to the reader 1304 may include data stored in the event log of the tag 1302. At step 1336, the transferred data is received and validated by the reader 1304.

Method 1300 may conclude as the tag 1302 and the reader 1304 enter an additional application phase at step 1338. As described above, application-specific actions may include, but are not limited to, actions such as advancing state machines and storing data. In some embodiments, the tag 1302 and the reader 1304 may follow the additional application phase by returning to the shutdown state and the pinging state respectively. In some embodiments, the combination of the LF and the HF phases is advantageous because the communications between the tag 1302 and the reader 1304 avoid interference with other frequency ranges while achieving required bandwidth. In addition, this mode of operation consumes power efficiently, as the tag 1302 is able to transfer large amounts of data during the short period of time the tag 1302 is operating in a high power, HF state.

Figure 14:
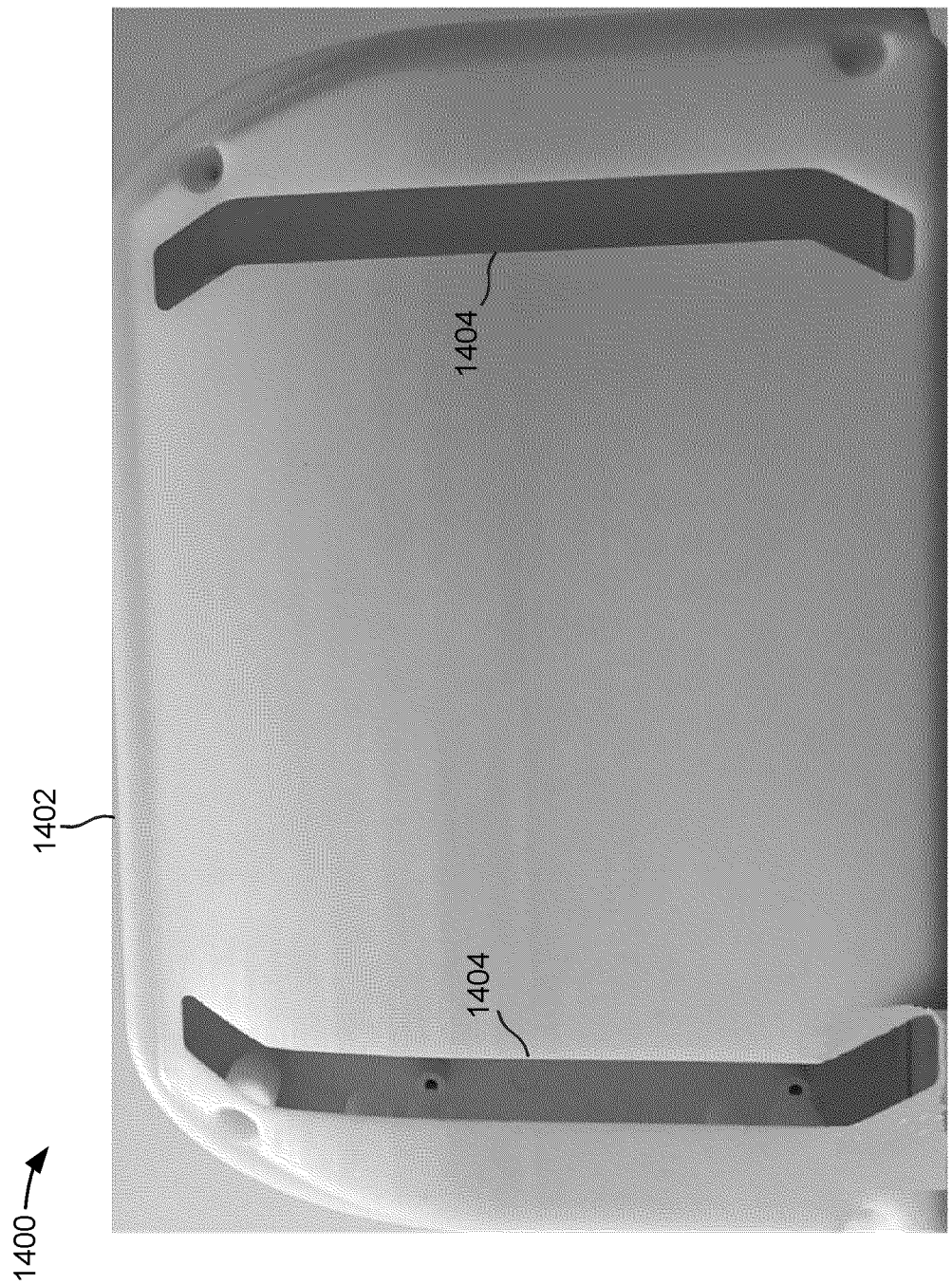
FIG. 14 is a schematic diagram of a visual monitoring system device, according to some embodiments.

Referring now to FIG. 14, a schematic diagram of a visual monitoring system device 1400 is depicted. In some embodiments, device 1400 is identical or substantially similar to visual monitoring system 734, described above with reference to FIGS. 7-8. As shown, the device 1400 includes a housing 1402 with two C-shaped openings 1404. An array of IR emitters (e.g., LEDs) and IR detectors may be arranged within the C-shaped openings 1404. In other embodiments, the openings 1404 may have any other suitable shape.

All processing for the visual monitoring system device 1400 may be performed using a low power embedded processor. In some embodiments, the embedded processor may be an ARM Cortex M4 device with 64 KB of program and/or data RAM and 512 KB of flash RAM. These specifications permit the visual monitoring system device 1400 to operate in a wide variety of physical environments (e.g., industrial, automotive), at a lower cost than other visual monitoring systems.

A processed model of previous examples of handwashing activity can be loaded into the memory of the device 1400. The model can be "trained" for a single motion, or a set of motions. For example, the model can be trained using the movements of the WHO six step hand hygiene protocol, as described above with reference to FIG. 10. The device 1400 may be configured to detect a tag using any suitable method (e.g., method 1200 or method 1300, described above with reference to FIGS. 12 and 13). After detecting the tag, the device 1400 may transition from a tag detection state to an IR processing mode.

In the IR processing mode, the output of the IR emitters through the openings 1404 may be mechanically focused on an area of interest (i.e., the location of a user's hands while completing a hand hygiene operation). Data in the form of IR emitter output and IR detector reflections based on movements in the area of interest may be provided to the processor using a GPIO/I2C serial protocol input.

In real time, the captured IR data is processed by a commercially-available machine intelligence library to compare the incoming data with the model library loaded in the flash memory of the processor and to determine a level of fit of the incoming data to the model. In some embodiments, the captured IR data is in the form of a stream of numbers which represent reflected infrared light from movement received by the detectors. The machine intelligence may also be utilized to train and build the model library using machine learning. In some embodiments, the model library may implement a support vector machine employing a n>1 degree polynomial kernel. In other embodiments, other classifier types may be employed depending on the type of movement to be measured. Both the data model and the classifier can be modified to suit a particular application (e.g., a particular hand washing protocol). Valid model fits may be scored on a continuous basis, and a complete set of data samples may be processed and scored at least every 300 ms.

If enough valid scores are achieved to determine that the targeted hand motions of the application have been made in a configurable period of time, the motions are marked by the processor as "occurred." Once a sufficient number and type of motions have been marked as "occurred," the hygiene operation may be marked as successful by the processor and stored in an event log of the device 1400. In some embodiments, the user may be informed of the successful event through the use of LED indicators, or an LED screen (e.g., feedback display 732, described above with reference to FIG. 8). In other embodiments, the user may not be informed of the successful event.

In some embodiments, the visual monitoring device 1400 may be configured to use gesture recognition to measure a user's compliance to hand hygiene guidelines in both duration and movement. Use of the IR emitters and detectors in combination with the embedded machine intelligence permits more efficient determination of the movements of the hand hygiene operation than visible light camera and accelerometer-based hand hygiene compliance systems. In other embodiments, the visual monitoring device 1400 could be used in applications other than hand hygiene compliance. For example, the visual monitoring device 1400 could be used in automotive applications to activate dashboard controls, or to assist drivers with reduced mobility by permitting finger gestures on the steering wheel to control automotive functions (e.g., switching on windshield wipers, activating a turn signal).

CONFIGURATION OF EXEMPLARY EMBODIMENTS

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A hand hygiene monitoring system, comprising:
   a wearable tag device configured to be coupled to a user; and
   a reader device communicably coupled to the wearable tag device;
   wherein the reader device is configured to:
   detect a presence of the wearable tag device by receiving a first frequency message comprising a user identifier of the user from the wearable tag device via near field magnetic induction (NFMI), wherein the reader device periodically transmits a detection message at a predetermined time interval using the first frequency to receive the first frequency message; and
   after detecting the presence of the wearable tag device:
   transmit a second frequency message using a second frequency to the wearable tag device requesting information associated with a hand hygiene operation, the second frequency having a higher frequency than the first frequency;
   receive the information associated with the hand hygiene operation performed by the user from the wearable tag device at the second frequency in response to receiving the second frequency message; and determine whether the wearable tag device has logged a compliant wash station encounter within a configurable time period based on the information; and wherein the reader device stores an encounter success event in a reader event log in response to a determination that the wearable tag device has logged the compliant wash station encounter within the configurable time period and transmits the encounter success event in the reader event log to a cloud server using cellular communications.

2. The hand hygiene monitoring system of claim 1, wherein the first frequency ranges from 30 KHz to 10 MHz.

3. The hand hygiene monitoring system of claim 1, wherein the second frequency ranges from 1.9 GHz to 2.1 GHz.

4. The hand hygiene monitoring system of claim 1, wherein the reader device is coupled to a threshold of at least one of a patient room, a bathroom, or a kitchen.

5. The hand hygiene monitoring system of claim 1, wherein the reader device comprises a flexible mat located proximate to a patient bed.

6. A method of monitoring hand hygiene, comprising:
   detecting, by a reader device, a presence of a wearable tag device configured to be coupled to a user;
   receiving, by the reader device, from the wearable device via near field magnetic induction (NFMI), a first frequency message comprising a user identifier of the user, wherein the reader device periodically transmits a detection message at a predetermined time interval using a first frequency to receive the first frequency message;
   after receiving the first frequency message:
   transmitting, from the reader device to the wearable tag device, a second frequency message using a second frequency requesting information associated with a hand hygiene operation, the second frequency having a higher frequency than the first frequency;
   receiving, by the reader device from the wearable device, the information associated with the hand hygiene operation performed by the user at the second frequency in response to receiving the second frequency message; and
   determining, by the reader device, whether the wearable tag device has logged a compliant wash station encounter within a configurable time period based on the information;
   wherein the reader device stores an encounter success event in a reader event log in response to a determination that the wearable tag device has logged the compliant wash station encounter within the configurable time period and transmits the encounter success event in the reader event log to a cloud server using cellular communications.

7. The method of claim 6, wherein the reader device is coupled to a threshold of at least one of a patient room, a bathroom, or a kitchen.

8. The method of claim 6, wherein the first frequency ranges from 30 KHz to 10 MHz.

9. The method of claim 6, wherein the second frequency ranges from 1.9 GHz to 2.1 GHz.

10. The method of claim 9, wherein the reader device comprises a flexible mat located proximate to a patient bed.

11. A hand hygiene monitoring system for a surgical setting, comprising:
    a wearable tag device configured to be coupled to a user; and
    a reader device communicably coupled to the wearable tag device; wherein the reader device is configured to:
    detect a presence of the wearable tag device by receiving a first frequency message comprising a user identifier of the user from the wearable tag device via near field magnetic induction (NFMI), wherein the reader device periodically transmits a detection message at a predetermined time interval using the first frequency to receive the first frequency message; and
    after detecting the presence of the wearable tag device:
    transmit a second frequency message using a second frequency to wearable tag device requesting user identification data and/or user-associated data stored in a memory device of the wearable tag device, the second frequency having a higher frequency than the first frequency;
    receive, by the reader device and from the wearable tag device, the user identification data and/or user-associated data at the second frequency in response to receiving the second frequency message;
    detect, by the reader device, hand movements of the user during a hand hygiene operation using at least one infrared movement detectors;
    determine, by the reader device, a real-time compliance status of the hand hygiene operation performed by the user based on the detected hand movements being compliant with a best practice hand movement; and
    in response to the real-time compliance status being compliant with the best practice hand movements, determine, by the reader device, a duration of the hand hygiene operation from the detected hand movements of the user; and
    transmit, by the reader device, data to a cloud server using cellular communications in a determination that the duration of the hand hygiene operation was sufficient.

12. The hand hygiene monitoring system of claim 11, wherein the reader device is coupled to a scrub station of a surgical scrub sink.

13. The hand hygiene monitoring system of claim 11, wherein the reader device is coupled to a hand sanitizer dispenser.

14. The hand hygiene monitoring system of claim 11, wherein the reader device further comprises a feedback display configured to display the best practice hand movement of the hand hygiene operation.

15. The hand hygiene monitoring system of claim 14, wherein the feedback display is further configured to display the detected hand movements of the user.

16. The hand hygiene monitoring system of claim 11, wherein the first frequency ranges from 30 KHz to 10 MHz.

17. The hand hygiene monitoring system of claim 11, wherein the second frequency ranges from 1.9 GHz to 2.1 GHz.

* * * * *